(12) United States Patent
Acquista et al.

(10) Patent No.: US 12,053,302 B2
(45) Date of Patent: *Aug. 6, 2024

(54) SYSTEM AND METHOD FOR MONITORING CONDITIONS OF A SUBJECT BASED ON WIRELESS SENSOR DATA

(71) Applicant: Peerbridge Health, Inc., New York, NY (US)

(72) Inventors: Angelo Joseph Acquista, New York, NY (US); Keith Sproat, Truckee, CA (US); Steven Geyster, Milton, MA (US); Arthur Bertolero, New York, NY (US); Leung-Hang Ma, Brooklyn, NY (US); John Shambroom, Framingham, MA (US); Benjamin Mughal, Des Moines, IA (US); Robert Joseph Bouthillier, Franklin, MA (US); Michael Peter Fusaro, Greenville, RI (US); Elisabeth Goodrich, Roslindale, MA (US)

(73) Assignee: Peerbridge Health, Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/297,966

(22) Filed: Apr. 10, 2023

(65) Prior Publication Data
US 2023/0240614 A1 Aug. 3, 2023

Related U.S. Application Data

(63) Continuation of application No. 15/454,528, filed on Mar. 9, 2017, now Pat. No. 11,622,722.
(Continued)

(51) Int. Cl.
A61B 5/00 (2006.01)
A61B 5/25 (2021.01)
(Continued)

(52) U.S. Cl.
CPC .......... *A61B 5/6833* (2013.01); *A61B 5/0015* (2013.01); *A61B 5/25* (2021.01);
(Continued)

(58) Field of Classification Search
CPC ......... A61B 5/6833; A61B 5/305; A61B 5/25; A61B 5/0015; A61B 5/6805;
(Continued)

(56) References Cited

U.S. PATENT DOCUMENTS 5,042,499 A 8/1991 Frank et al.
5,545,154 A 8/1996 Oberholtzer
(Continued)

FOREIGN PATENT DOCUMENTS

CN 102525455 A 7/2012
CN 104510464 A 4/2015
(Continued)

OTHER PUBLICATIONS

International Search Report and Written Opinion; PCTUS17/21539; Mailed Jun. 26, 2017.
(Continued)

*Primary Examiner* — Eun Hwa Kim
*Assistant Examiner* — Catherine Premraj
(74) *Attorney, Agent, or Firm* — Dunlap Bennett & Ludwig, PLLC

(57) ABSTRACT

A system for wirelessly obtaining physiological data from a subject includes a sensor patch and a separate electronics package. The sensor patch is disposed on and adheres to the subject, and includes a first part of a releasable electrical connector. An electronics package includes a second part of the first releasable electrical connector, which is used to physically and electrically connect the electronics package to the sensor patch. The electronics package includes a flexible substrate, with shells set on this substrate. The shells
(Continued)

enclose the electronics. The shells are connected by a flexible circuit board. Analog front end circuitry is placed in one shell, while the wireless transceiver is placed in the other shell.

19 Claims, 25 Drawing Sheets

Related U.S. Application Data

(60) Provisional application No. 62/305,854, filed on Mar. 9, 2016.

(51) Int. Cl.
*A61B 5/305* (2021.01)
*H01R 31/00* (2006.01)
*H05K 1/18* (2006.01)
*H05K 3/28* (2006.01)
*H05K 3/32* (2006.01)

(52) U.S. Cl.
CPC ............. *A61B 5/305* (2021.01); *H01R 31/00* (2013.01); *H05K 1/189* (2013.01); *A61B 5/6805* (2013.01); *A61B 2503/10* (2013.01); *H05K 3/284* (2013.01); *H05K 3/326* (2013.01); *H05K 2201/10098* (2013.01); *H05K 2201/10151* (2013.01)

(58) Field of Classification Search
CPC .... A61B 2506/10; H01R 31/00; H05K 1/189; H05K 3/284; H05K 3/326; H05K 2201/10098; H05K 2201/10151
See application file for complete search history.

(56) References Cited

U.S. PATENT DOCUMENTS

| | | | |
|---|---|---|---|
| 5,591,820 | A | 1/1997 | Kydonieus et al. |
| 2008/0305154 | A1 | 12/2008 | Yanaki |
| 2009/0088614 | A1 | 4/2009 | Taub |
| 2011/0001497 | A1* | 1/2011 | Chetelat .................. A61B 5/30 324/692 |
| 2013/0060098 | A1 | 3/2013 | Thomsen et al. |
| 2013/0231546 | A1 | 9/2013 | Choe et al. |
| 2013/0331665 | A1* | 12/2013 | Libbus .................. A61B 5/443 600/509 |
| 2014/0187976 | A1 | 7/2014 | Banet et al. |
| 2015/0057512 | A1 | 2/2015 | Kapoor |
| 2015/0094557 | A1 | 4/2015 | Hsu et al. |
| 2015/0164324 | A1 | 6/2015 | Russell |
| 2015/0238107 | A1 | 8/2015 | Acquista et al. |

FOREIGN PATENT DOCUMENTS

| | | |
|---|---|---|
| CN | 105050495 A | 11/2015 |
| CN | 105377127 A | 3/2016 |
| WO | 2008153931 A2 | 12/2008 |
| WO | 2015113054 A1 | 7/2015 |

OTHER PUBLICATIONS

Chinese Office Action; 202111527892.7; Published Sep. 20, 2023.
European Search Report; 23173778.4; Dated Feb. 16, 2024.
European Search Report; 23173778.4; Dated Oct. 16, 2023.

* cited by examiner

SYSTEM AND METHOD FOR MONITORING CONDITIONS OF A SUBJECT BASED ON WIRELESS SENSOR DATA

CROSS-REFERENCE TO RELATED APPLICATIONS

This application is a continuation of U.S. Pat. No. 11,622,722, filed Mar. 9, 2017 and issued on Apr. 11, 2023, which in turn claims priority to U.S. Provisional Application Ser. No. 62/305,854, filed on Mar. 9, 2016, the entire disclosure of both of which is incorporated herein by reference.

FIELD OF THE INVENTION

Various embodiments of the present invention relate to a wireless sensor that offers convenient use for a subject, such as a patient, in the monitoring, in real time (or quasi-real time), of a medical signal, such as a hemodynamic parameter. In addition, various embodiments of the present invention also relate to methods for aligning data from different wireless sensors with each other, with another device, or both.

BACKGROUND

Monitoring various vital signs of a patient has been an important aspect of hospital patient care, especially for patients with diseases at advanced stages, suffering from severe trauma, or in other emergency settings. Additionally, outpatient monitoring of various physiological conditions are being increasingly used for evaluation of patient health conditions as well as early detection and treatment of heart diseases, diabetes, and other diseases. For example, an electrocardiogram (ECG or EKG) can be used to evaluate the heart condition of a patient, where electrodes are placed at certain locations on the chest, arms, and/or legs. These electrodes can be connected to an ECG machine by lead wires, and the electric signals received by the ECG machine can be analyzed and displayed for the physician's information and further interpretation.

Attempts have also been made to develop systems to improve a patient's comfort, freedom and privacy by decreasing the number and volume of devices directly or indirectly attached to the patient. For example, U.S. Pat. No. 7,979,111 discloses a wireless electrode arrangement and method for patient monitoring, where a plurality of wireless electrodes suitable for attachment to the surface of the body of a patient are capable of continuously monitoring of a subject wirelessly. U.S. Pat. No. 9,101,264 and co-pending U.S. patent application Ser. No. 14/216,174 (published as U.S. Patent Application Publication No. 20140275928) further describe a network of wireless sensors for monitoring hemodynamic parameters of a subject. The disclosures of all of these documents are incorporated herein by reference in their entireties.

Implantable devices such as implantable cardioverter defibrillators (ICDs) or pacemakers are often indicated for patients who have or are at increased risk for various heart conditions related to the heart's electrical system, such as ventricular and atrial arrhythmias including but not limited to ventricular fibrillation, ventricular tachycardia, atrial fibrillation, and bradycardia, etc. These implantable devices can monitor and/or manage certain heart conditions of the patients and prevent or control heart episodes that would otherwise interfere with daily life or be life threatening, and can therefore allow patients with certain heart conditions to carry on their normal lives with relatively few restrictions and generally low level of discomfort. However, these invasive devices cater primarily to patients who are at an advanced stage of disease.

Additionally, there can be limiting factors for these implantable devices such as inaccuracy in detecting the relevant heart condition episodes and administering appropriate therapies. For example, the positioning and contact of the leads of the ICDs with the heart muscle can be affected by the patient's movement, and the problem is more acute for young and more active patients. ICDs can also have lead failures after being worn by a patient for an extended period of time, e.g., a number of years. Lead positioning errors and failures can cause inaccurate or distorted electrograms, and may thereby lead to insufficient, overly aggressive, or otherwise inappropriate cardiac intervention, such as excessive number of unwarranted shocks or shocks with unnecessarily large magnitude, which can cause discomfort, pain, and other undesirable effects on the quality of life of the patients.

There is a need for a system that integrates the real time monitoring capability of wireless sensors worn by a patient that is accurate and convenient for the patient to use and replace. Ideally, such devices should be suitable not only for patients who are at an advanced stage of a disease condition, but also for relatively healthier subjects that nonetheless desire monitoring of a physiological condition. Further, there is a need to ensure accurate synchronization between such devices to facilitate the collection of medically-relevant sensor information data.

SUMMARY OF THE INVENTION

In one aspect, an electrode patch is disclosed that includes a first electrode configured to contact a subject, a first part of a first releasable electrical connector coupled to the first electrode and configured to releasably connect to a second part of the first releasable electrical connector, a first adhesive layer having an opening, with the first electrode disposed within the opening, and a first protective layer disposed over and covering the first adhesive layer. The first protective layer includes an opening corresponding to the first releasable electrical connector. In a preferred embodiment, the first part of the first releasable electrical connector is adhered to the first electrode, the first electrode is made from hydrogel and the first adhesive layer is made from hydrocolloid. The first part of the first releasable electrical connector may extend through the opening in the first protective layer. A bottom surface of the first protective layer is preferably adhesive for adhering to a subject. The first protective layer may be made from, for example, polyurethane with a moisture vapor transmission rate of 300 to 1400 gm/m2/day.

In certain embodiments of the electrode patch, a first backer is disposed over the opening of the first adhesive layer and over at least a portion of the first adhesive layer to provide structural strength. The backer includes an opening corresponding to the first part of the first releasable electrical connector. In a specific embodiment, the first part of the first releasable electrical connector is formed from a top portion coupled to a bottom portion, and the backer is sandwiched between the top portion and the bottom portion. In specific embodiments the backer is formed from perforated polyethylene terephthalate or an ethylene-vinyl acetate/polyethylene blend.

In a specific embodiment, the electrode patch can further include a second electrode configured to contact the subject, a first part of a second releasable electrical connector physically and electrically coupled to the second electrode, a second adhesive layer with an opening, the second electrode disposed within the opening, and a second protective layer disposed over and covering the second adhesive layer, in which the second protective layer has an opening corresponding to the second releasable electrical connector. In one variation, the first protective layer and the second protective layer are contiguous and are frangibly connected to each other via a perforation. In another variation, the first protective layer and the second protective layer are not contiguous, and the electrode patch further includes a release liner disposed over respective top surfaces of the first protective layer and the second protective layer to hold them in alignment with each other. In yet another variation, an isolating barrier, such as closed-cell foam, is disposed between the first adhesive layer and the second adhesive layer. A bottom surface of the isolating barrier may be configured to adhere to the subject.

In another aspect, a method is disclosed for obtaining physiological data from a subject. A sensor patch is first disposed on the subject. The sensor patch adheres to the subject and includes a first part of a first releasable electrical connector, which is electrically coupled to a sensor of the sensor patch, and which is configured to releasably connect to a second part of the first releasable electrical connector. Then, an electronics package is electrically and physically connected to the sensor patch. The electronics package includes the second part of the first releasable electrical connector for such electrical and physical connection. This second part is electrically coupled to electronics of the electronics package, which are configured to monitor the sensor to generate corresponding physiological data and to wirelessly transmit the corresponding physiological data to another device.

In one embodiment, the sensor patch includes a plurality of sensors, such as electrodes, held in a predetermined geometrical arrangement by a release liner. In such embodiments, the method further includes removing the release liner after disposing the sensor patch on the subject and prior to coupling the electronics package to the sensor patch.

In yet another aspect, an electronics package for a wireless physiological sensor system is disclosed. The electronics package includes a substrate. A first part of a first releasable electrical connector is connected to the substrate and configured to releasably connect to a second part of the first releasable electrical connector disposed on a sensor patch. A first shell is disposed on the substrate, such as over the first part of the releasable electrical connector. A second shell is also disposed on the substrate. Finally, the electronics package includes electronics configured to monitor at least one sensor of the sensor patch to generate corresponding physiological data and to wirelessly transmit the corresponding physiological data to another device. The electronics include a first electronics sub-system disposed in the first shell and electrically connected to the first part of the first releasable electrical connector, a second electronics sub-system disposed in the second shell, and a first flexible circuit, such as a flexible circuit board, electrically connecting the first electronics sub-system to the second electronics sub-system. The electronics also preferably includes at least one rechargeable battery.

To accommodate, for example, movement of the subject, in preferred embodiments the substrate is preferably flexible, the first electronics sub-system is flexibly connected to the first part of the first releasable electrical connector, and a length of the first flexible circuit between the first shell and the second shell is substantially greater than a corresponding distance between the first shell and the second shell.

In some embodiments, at least a portion of the first shell and at least a portion of the first part of the first releasable electrical connector are disposed in the substrate.

In preferred embodiments, to avoid electrical interference, the first electronics sub-system comprises analog front end circuitry to obtain signals from the at least one sensor and the second electronics sub-system comprises a wireless transceiver to wirelessly transmit the corresponding physiological data.

In a specific embodiment, at least three sensors are arranged in a substantially L shaped configuration on the sensor patch, and the electronics package further includes a third shell disposed on the substrate, a third electronics sub-system disposed in the third shell. A second flexible circuit electrically connects the third electronics sub-system to the second electronics sub-system. Also, a first part of a second releasable electrical connector is connected to the substrate, with the second electronics sub-system electrically connected to the first part of the second releasable electrical connector. Similarly, a first part of a third releasable electrical connector is connected to the substrate and electrically connected to the third electronics subsystem. In such embodiments, the first shell, second shell and third shell may be arranged in a substantially L-shaped configuration on the substrate corresponding to the at least three sensors, and in particular corresponding to second parts of the first, second and third releasable electrical connectors on the sensor patch to mechanically and electrically couple the electronics package to the sensor patch.

In a particular refinement, such as when the sensors are electrodes, and to provide for clean signal collection from the sensors, the first flexible circuit can include a first signal line extending between the first shell and the second shell. Similarly, the second flexible circuit includes a second signal line extending between the second shell and the third shell. The first flexible circuit also includes a first open electrical line electrically connected to the second signal line and extending along the first signal line, while the second flexible circuit further includes a second open electrical line electrically connected to the first signal line and extending along the second signal line.

In various embodiments the first flexible circuit is at least partially disposed within the substrate, and the first flexible circuit includes a contact region exposed from the substrate, which can be used, for example, as a port for recharging, programming or data collection purposes.

BRIEF DESCRIPTION OF THE DRAWINGS

The various aspects and embodiments disclosed herein will be better understood when read in conjunction with the appended drawings, wherein like reference numerals refer to like components. For the purposes of illustrating aspects of the present application, there are shown in the drawings certain preferred embodiments. It should be understood, however, that the application is not limited to the precise arrangement, structures, features, embodiments, aspects, and devices shown, and the arrangements, structures, features, embodiments, aspects and devices shown may be used singularly or in combination with other arrangements, structures, features, embodiments, aspects and devices. The drawings are not necessarily drawn to scale and are not in any way intended to limit the scope of this invention, but are merely presented to clarify illustrated embodiments of the invention. In these drawings.

DETAILED DESCRIPTION

Figure 1:
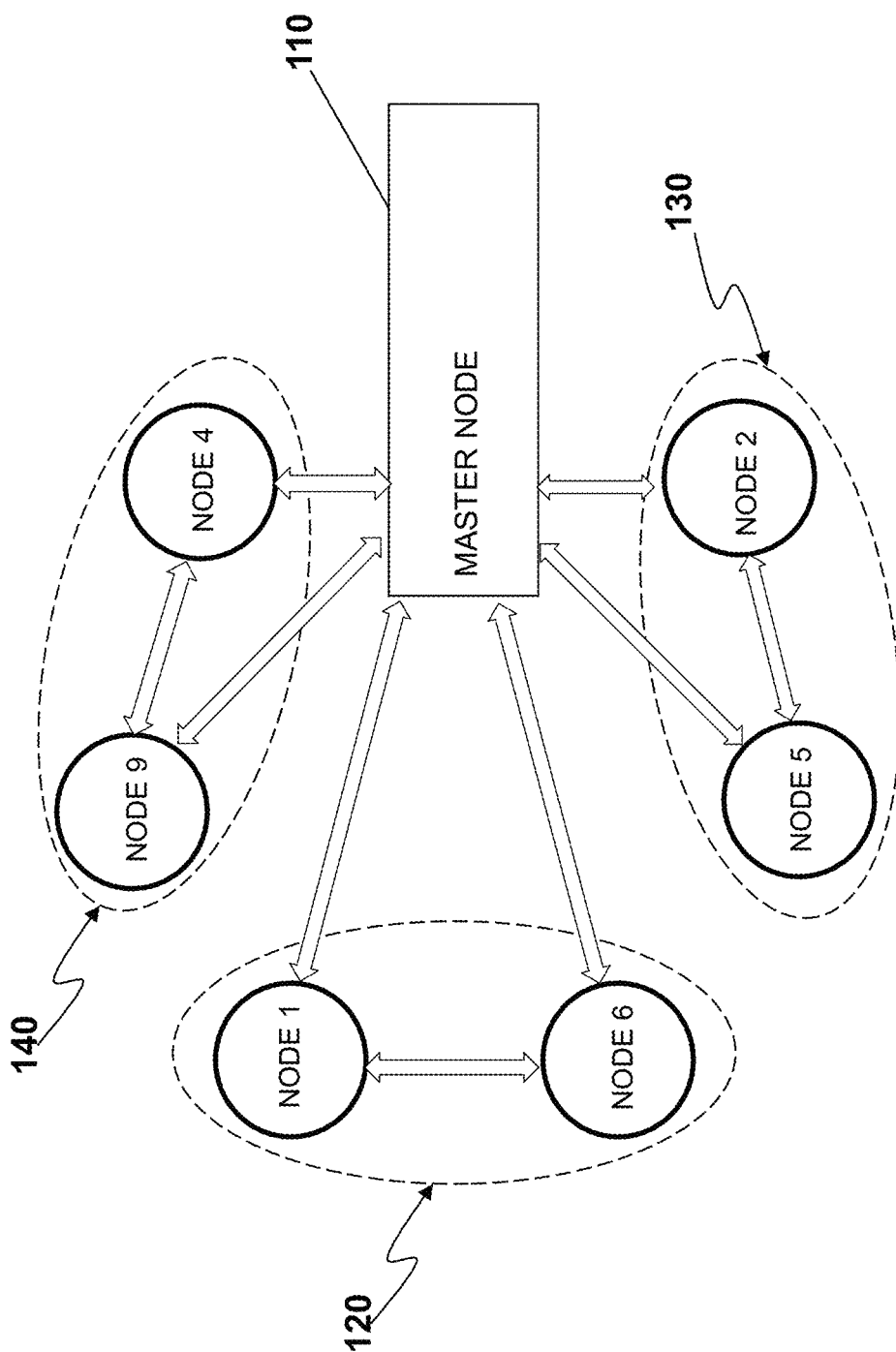
FIG. 1 illustrates a network formed by a plurality of sensors according to an embodiment of the invention.

Certain embodiments of the present invention will now be discussed with reference to the aforementioned figures. In one embodiment, the present invention provides a wireless sensor suitable for attachment to the skin of a subject. The sensor can form a network with similar sensors, and the data collected from these sensors can be synchronized or aligned in the time domain. The type of network may utilize a routing topology include: star, mesh, pseudo-mesh network, or any other routing topology. Each of the sensors can include a sensing component configured to detect a signal corresponding to at least one physiological condition of the subject, and a communication component configured to wirelessly transmit the detected signal to either another wireless sensor or an external monitoring device. The external monitoring device may be local to the patient, such as a cellular telephone, tablet computer or other type of computing device, or may be remote, such as an Internet server, and may serve as a master node for the network. The communication component of selected sensors can also be configured to receive and/or relay signals transmitted from other wireless sensors.

As described herein, a wireless sensor includes a sensing component configured to detect a signal corresponding to a physiological condition, such as vital signs including (but certainly not limited to) hemodynamic parameters of a subject, such as, but not limited to, a hospital patient. Hemodynamics, as known in the art, relates to the study of blood flow. The circulatory system, including the heart, the arteries, the microcirculation, and the vein, functions to transport the blood to deliver $0_2$, nutrients and chemicals to the cells of the body, and to remove the cellular waste products. The heart is the driver of the circulatory system generating cardiac output (CO) by rhythmically contracting and relaxing. This creates changes in regional pressures, and, combined with a complex valvular system in the heart and the veins, ensures that the blood moves around the circulatory system in one direction. Hemodynamic parameters (or properties), as described herein, include the physiological conditions associated with the blood flow, which includes not only the physical characteristics of the blood flow itself, e.g., blood flow rate, blood flow pressure, temperature, and pulse rate, but also those parameters relating to the blood components such as cells, proteins, chemicals, etc.

The vital signs to be monitored as contemplated in the disclosed embodiments can include, but are not limited to, ECG (electrocardiogram), EEG (electroencephalogram), EMG (electromyogram), EOG (electrooculogram), ERG (electroretinogram), temperature, pulse oximetry, oxygen saturation, oxyhemoglobin saturation, blood component concentration (e.g., glucose level, lipid level, cholesterol level, triglyceride level, levels of different salts, concentration of different types of cells, concentration of blood proteins such as thrombin, cancer markers, heart failure markers), renal function test components (e.g., concentration of albumin, urea, and creatinine in the urine), liver function test components, organ functions, blood pressure (such as atrial pressure, ventricular pressure, pulmonary artery pressure, systolic pressure, diastolic pressure, etc.), blood velocity, respiration rate, pulse rate, (end tidal) CO2 level, blood drug concentration, organic or inorganic substance concentration in the blood (e.g. uric acid, vitamins, heavy metals, carbon monoxide, bacterial toxin), cardiac output, heart rate, heart rhythm, heart rate variability, pH, pathogens, motion, weight, etc. Additionally, the system can be used to monitor migraines, a subject's galvanic skin response, and responses to electrical nerve and muscle stimulation, etc. Depending on the types of underlying physiological conditions to be monitored, the sensing component can include, but is not limited to, an electrochemical detector (such as an needle electrode galvanic electrode or a band electrode for detecting a surface potential or current), an electromagnetic detector (e.g., an optical detector such as an infrared detector and visible light detector, as well as an x-ray detector, gamma-ray detector, etc.), a thermal detector, a pressure detector, an ultrasonic detector, a chemical detector, a magnetic detector, an x-ray detector, an accelerometer, a gyrometer, a motion detector, etc. Other detectors in emerging sensor technology, such as laser Doppler, paper sensors, sensor tattoos, etc., can also be used.

Further, each wireless sensor includes a communication component configured for wireless communication with other sensors, an external monitoring device (e.g., master node) or both. For example, the wireless electrodes described in U.S. Pat. No. 7,979,111, which is incorporated herein by reference, including the transmitting circuit, such as the remote telemeter, can be such a wireless sensor. A wireless sensor can include a mote as described in the above patent, or can include a fully integrated and functional communication circuit that includes an amplifier, a processor, a memory, a battery, and an RF module. Each or selected ones of the wireless sensors can further include a memory of suitable size (for example, 4 GB or 8 GB, to store a large volume or size of relevant medical records of a subject), a data processor, power supply, etc.

In some embodiments, the wireless sensors form a mesh network, where each sensor (also referred to as a "node", "sensor node" or "regular node" hereinafter) not only captures and disseminates its own data, but may also serve as a relay for other nodes, that is, the nodes in the mesh network collaborate with each other to propagate the data in the network. In certain embodiments, the mesh network further includes one or more control nodes (or master nodes), which communicate with selected or all of the regular nodes. The master nodes can serve as a data acquisition, processing, and command center. In other embodiments, the wireless sensors communicate only with each other, e.g., for purpose of synchronizing signal acquisition. In further embodiments, the wireless sensors communicate only with an external control node, but do not communicate with each other or form a mesh network.

The wireless sensors or the network of the wireless sensors can continuously monitor selected physiological data of the subject, and communicates the signals acquired from the sensing components via the communicating components of the sensors to a control or master node. Each of the wireless sensors can be programmed such that signals detected by the sensor falling into a predetermined (e.g., an acceptable or normal) range are not transmitted, or transmitted at a lower frequency. The acceptable range for signals for different subjects and for each wireless sensor can be set individually, for example, based on the type of the sensor, the subject's condition, the therapy being used by the subject, etc. A control or master node can include a communication component configured to wirelessly receive signals from each of the plurality of wireless sensors, and send data and/or commands to each of the plurality of wireless sensors. The control or master node can further include a monitoring unit coupled with the communication component. For example, the monitoring unit can include a readable medium and a processor coupled to the computer readable medium. The computer readable medium can store coded instructions for execution by the computer processor, which, upon the execution of the instructions, carries out pre-designed tasks.

In some embodiments, the master node of a mesh network can be a PC or workstation computer equipped with a communication component, such as a dongle, for communicating with the wireless sensors. The master node can also include a portable device having a processor, a memory, a display and/or other audiovisual output capabilities to present information to a user, and capabilities of wirelessly communicating with the wireless sensors. In other examples, the master node can include a commercial portable computing device, such as a smart phone (e.g., an iPhone, an Android-based phone, a Windows Mobile-based phone, etc.), a tablet (such as an iPad, a Samsung Galaxy Tab, Google Nexus 7 or 10, etc.), or other similar devices. In further examples, the control and communication capabilities of a master node can also be implemented on one or more regular nodes to "upgrade" such regular nodes into "super nodes" that include both sensing capabilities and the functionalities of a master node. For example, in some embodiments one or more of the nodes may include cellular and/or satellite telecommunications capabilities to establish communications with a remote server.

In the following, a wireless sensor including ECG electrodes suitable for acquiring electrophysiological signals related to cardiac function is used for illustrating the operating principles of the sensors and the network formed therefrom. In these sensors, each of the sensors include one or more electrodes which can acquire data related to the quality of the ECG signal, such as the amplitude of a detected voltage, a detected current, and/or electrical skin resistance, and transmit such data to other sensors or the master nodes.

For ECG applications, multiple wireless sensors may be employed, which are placed on the subject's body in predetermined locations. Preferably, these wireless sensors can self-configure into a set or group which wirelessly sends diagnostic quality ECG signals in a synchronous fashion to a master node, which can derive or synthesize ECG spectrum for display or other forms usable by a physician (or other users) based on the transmitted ECG signals. These sensors can also be configured to send and/or receive signals to/from the master node when a proximity criterion is satisfied, e.g., when the master node is within a predetermined distance from the wireless sensor, e.g., within 3 feet.

For illustration purposes and not limitation, a mesh or pseudo-mesh network formed by a plurality of sensors can be represented by a schematic block diagram as shown in FIG. 1. The illustrated network includes six sensor nodes and a single master node 110. The sensor nodes can be divided, for example, into three clusters: cluster 120 (including node 1 and node 6), cluster 130 (node 2 and node 5), and cluster 140 (node 4 and node 9). The arrows in FIG. 1 represent communication paths between the nodes. More generally, a cluster can be thought of as having one, two or more nodes. As depicted in this example, the network supports at least two modes of communication: (1) communication between the master node and each of the nodes, and (2) communication between nodes within a cluster. Such a configuration allows for the sensor nodes to make their own decisions and reconfigure the network independently of the master node 110. The wireless communication within the mesh network can be based on proprietary communication stacks utilizing the principles of time domain multiple access (TDMA), with frequencies selected from various MICS bands (Medical Implant Communications Service frequencies) or from the ISM (Industrial, Scientific, and Medical frequency bands (900 MHz, 2.4 GHz, or 5.8 GHz)) as would be appreciated by one of ordinary skill in the art.

For wireless sensors that are configured to detect ECG signals, examples of which are described herein, the sensors can be attached to the skin of a subject for ECG signals recordation in a manner that is similar to the configuration of traditional 3-lead, 5-lead, or 12-lead ECG leads. Signal acquisition between the nodes can be synchronized for processing of the ECG signals, as described later.

Figure 2A:
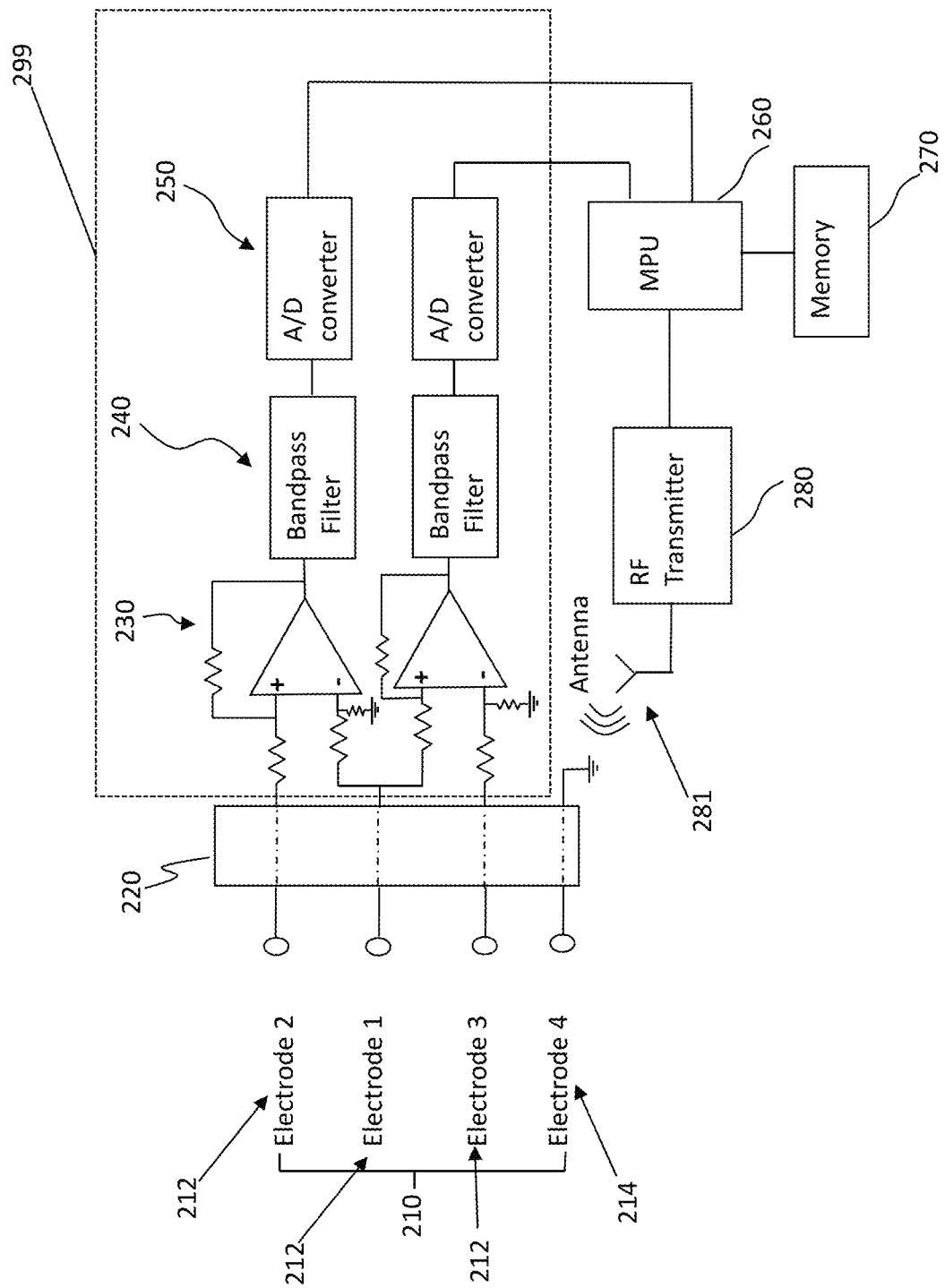
FIGS. 2A and 2B are logical block diagrams of a sensor according to an embodiment of the invention.

An example block diagram of the logical structure of an embodiment ECG sensor 200 is illustrated in FIG. 2. Four electrodes 210 are provided, including three signal electrodes 212 and an electronic ground electrode 214. These electrodes 212, 214 are connected to instrumentation amplifiers 230 via input protection circuit 220 that protect against electric shock and radio frequency interference. The instrumentation amplifiers 230 measure the difference between its two inputs and amplify that with a gain, e.g., of approximately 3.5. The gain of each amplifier 230 can be adjusted by way of the resistors, as known in the art, and are connected to the ground electrode 214 via a respective resistor or resistors, as known in the art. The amplified signals are optionally filtered by bandpass filters 240 (typically to the frequency response of 0.05 Hz to 60 Hz or alternatively 100 Hz or 150 Hz). Additional gain can optionally be provided in the bandpass filter stage to reach a total system gain of, for example, approximately 300. This results in, for example, an input range of approximately 10 m V between any pair of signal electrodes 212. However, it will be appreciated that the input range may also be adjustable, such as through hardware/firmware or software changes. The individual channel signals can then be digitized by A/D converters 250. The converters' resolution may be, for example, 12 bits or 16 bits. Or, the A/D converters 250 may have a higher native resolution, such as 24 bits, which is then down-converted to a lower resolution, such as 16 bits. Collectively, the amplifiers 230, band pass filters 240 and A/D converters 250, inter alia, are referred to as the analog front end 299 of the sensor 200, and may be provided by a discrete component, such as an ADS1293 from Texas Instruments, and the characteristics of each (gain, filtering, sampling rate, etc.) may be programmable, as known in the art. The digitized ECG signals from the analog front end 299 are passed through to a micro-processing unit (MPU) 260 for processing. The processed signals may be stored on board in a memory 270 coupled to the MPU 260, e.g., a flash memory, which can also store program code executable by the MPU 260 to control overall operations of the sensor 200. Additionally or alternatively, the processed signals can be sent to an RF transmitter 280 and transmitted via an antenna 281, or via a wired connection, such as USB, to, directly or indirectly, an external device (not shown), e.g., a smartphone, a tablet, a computer, another node, etc.

Figure 2B:
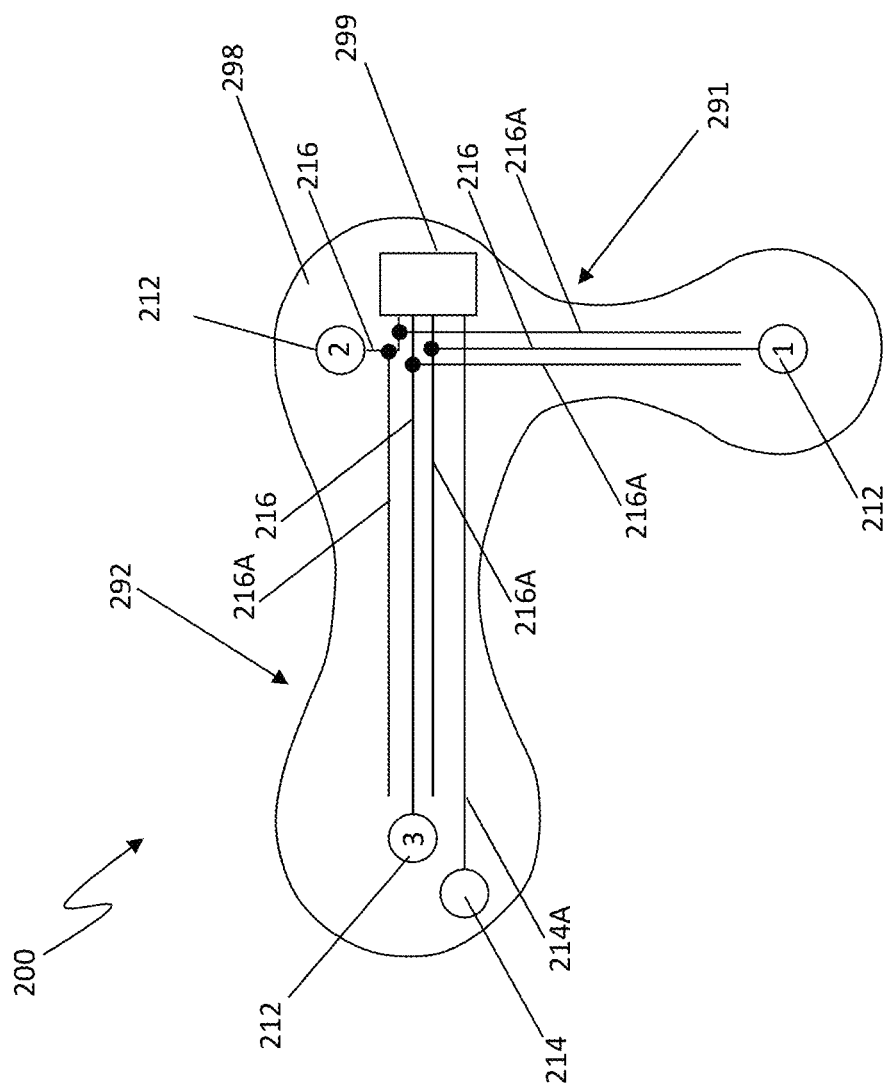

Because the sensor 200 may work in a diverse array of environments, many of which may be electronically noisy, it is desirable in various embodiments that noise cancellation techniques be employed in the sensor 200 in the analog front end 299. As shown in FIG. 2B, and discussed in more detail later, the analog front end 299 and electrodes 210 are mounted on a substantially L-shaped substrate 298, having a first arm 291 and a second arm 292 that is substantially perpendicular to the first arm 291, such as from 70° to 120° with respect to the first arm 291. Each signal electrode 212 is electrically connected to the analog front end 299 by way of a respective trace 216, while the electronic ground electrode 214 is electrically connected to the analog front end 299 by its own trace 214A. The three signal electrodes 212 are respectively located at the ends and intersection of the arms 291, 292. The ground electrode 214 may be located anywhere on the substrate 298, such as next to one of the signal electrodes 212 at the ends of the arms 291, 292.

The active traces 216 that electrically connect the signal electrodes 212 with the analog front end 299 pickup ECG signals from the body and also act as antennas and as such can pick up unwanted noise from the surrounding environment. To the extent that this noise is common to all of the signal electrodes 212, conventional common mode noise rejection techniques making use of the ground electrode 214 can be employed by the analog front end 299 to reduce this noise. It is therefore desirable that the noise captured in each channel through the signal electrodes 212 and corresponding traces 216 be as identical as possible with the noise on the other signal electrodes 212 and corresponding traces 216. Each trace 216 will optionally include at least one open lead 216A extending in a direction along trace 216, forming an overall trace that is substantially L-shaped to match the shape of the substance and the orientation of the electrodes. For example, other shapes may be advisable for different examples and active traces 216 and/or open leads 216A need not be in a straight line. Additionally there is minimal distance between the traces 216 and open leads 216A extending from each of the respective electrodes 212. In a circuit board configuration this distance is preferably between 0.4 and 4.4 mil. In other embodiment, this distance is preferably at least less than 1 cm.

For example, the trace 216 extending from a first signal electrode 212 "1" at the end of the first arm 291 includes and is electrically connected to a substantially perpendicular open lead 216A extending along the second arm 292 having a length that is preferably similar in length to the trace 216 for the third signal electrode 212 "3" at the end of the second arm 292. For example, that trace 216 is preferably between 2200 and 2600 mil, with a more preferred length of 2480 mil. That open lead 216A is preferably between 2500 and 3000 mil, with a more preferred length of 2875 mil. Similarly, the trace 216 for the third signal electrode 212 "3" at the end of second arm 292 includes and is electrically connected to an open lead 216A extending along the first arm 291 with a length that is preferably similar to that of the trace 216 of the first signal electrode 212 "1". For example, that trace 216 is preferably between 3000 and 3600 mil, with a more preferred length of 3310 mil. That open lead 216A is preferably between 2200 and 2800 mil, with a more preferred length of 2488 mil. The second signal electrode 212 "2" at the junction of the arms 291, 292 includes and is electrically connected to two such open leads 216A, substantially perpendicular to each other, running respectively along the first arm 291 with a length substantially equal to the trace 216 of the first signal electrode 212 "1" and along the second arm 292 with a length substantially equal to the trace 216 of the third signal electrode 212 "3". An additional trace 216 extending from the second signal electrode 212 "2" which like the other trace 216s can be L shaped and connect to analog front end 299 may also contain multiple open leads 216A extend in perpendicular directions. That trace 216 is preferably between 400 and 700 mil, with a more preferred length of 574 mil. One of such open leads 216A that are perpendicular to each other are preferably between 2500 and 3200 mil and more preferably 2962 mil while the other open lead 216A is preferably between 2000 and 2600 mil and most preferably 2305. Hence, the use of open leads 216A together with the active traces 216 make the noise picked up in each channel as common as possible, thus facilitating its rejection in the analog front end.

Figure 3:
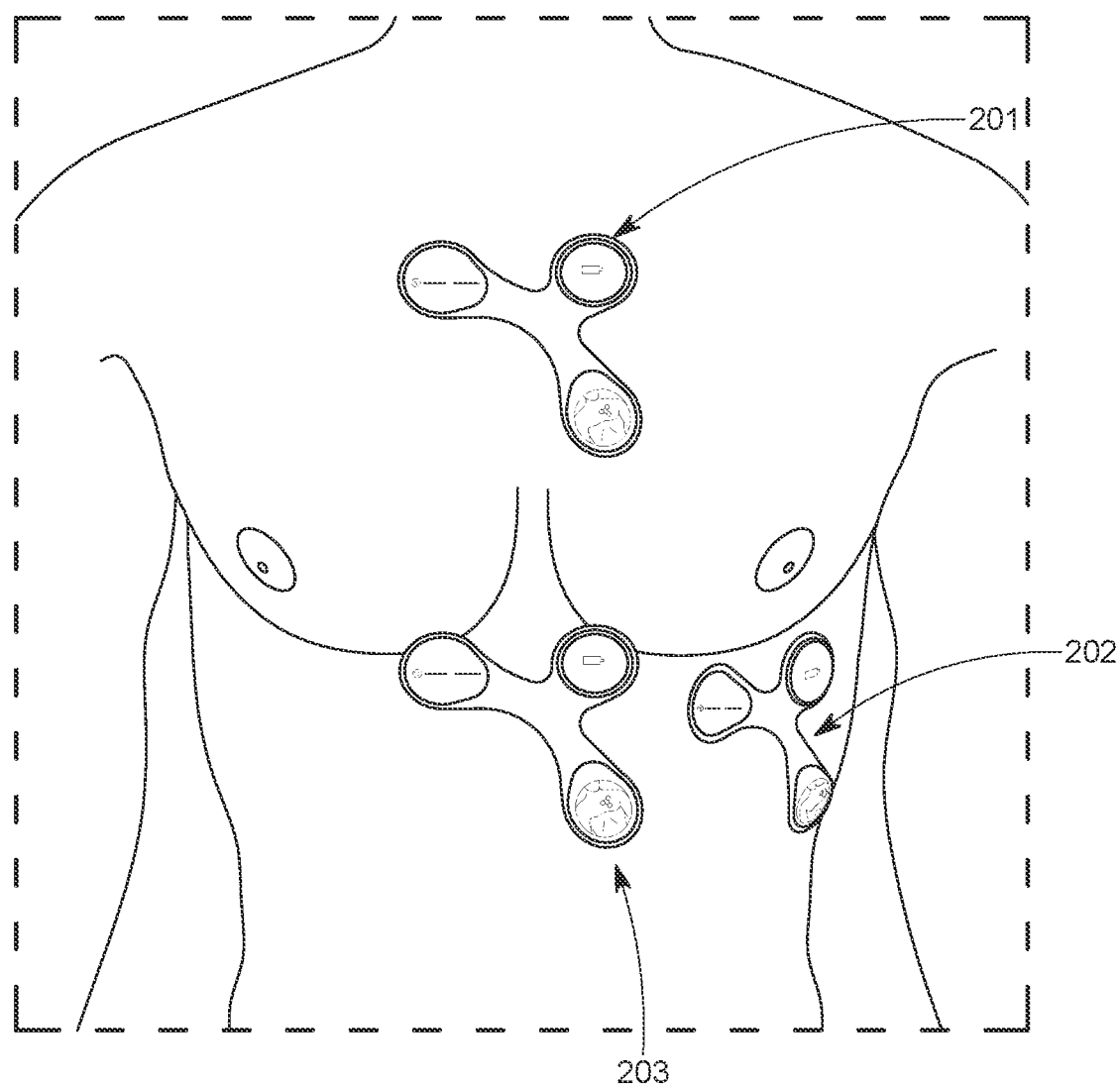
FIG. 3 depicts the placement of multiple sensors on a subject according to an embodiment of the invention.

In some embodiments, multiple surface nodes can be placed on the skin of the subject. As shown in FIG. 3, a first surface node 201 can be placed high on the sternum just below the clavicle. This can be advantageous for detection of atrial rhythm, as it is nearest the heart's atria, affording the best opportunity to monitor atrial fibrillation. There is less muscle in this location to contaminate the ECG with any electromyogram (EMG) artifact, and it can be on a tissue that is less likely to move and contaminate the ECG with motion artifact. An optional second surface node 202 may be added nearest to the ventricles. Two electrodes of this group can be at locations V4 and V5 of a standard 12-lead ECG, and the third a proxy for the left leg location. The signals from the two surface nodes may be combined in various ways to provide a faithful representation of a standard 3, 5, or 12 lead ECG. The second surface node 202 can also be able to measure ventricular ischemia due to blockage of the major vessels. An optional third tripole surface node 203 may be added to further facilitate the derivation of a full 12-lead ECG. Alternatively, a calibration step may be employed to derive the 12 lead ECG. This can be an internal calibration by temporarily connecting the two (or more) sensors electrically to calibrate, and then disconnected the sensors for the remaining of the operation. Alternatively, calibration can be done with an external device (e.g. a wired 12-lead ECG machine) to establish the baseline correlation between the wired and wireless data to facilitate downstream signal processing.

In a system where there are more than one wireless sensor, some or all of the wireless sensors can each individually transmit the collected physiological data to an external device (e.g., a monitoring device). Alternatively, one of the wireless sensors can include hardware and software necessary to serve as a master node or gateway that receives detected physiological data from other wireless sensors, and forward such signals via a radio or WiFi link to the external monitoring device at an appropriate rate (e.g., to save battery power of the sensors). The transmission can also be optionally compressed with little or no information loss. The transmitted physiological data can be processed by the monitoring device with appropriate program, or can be further uploaded to a server for processing and/or analysis, which are described further below. Signal acquisition of the various wireless sensors can also be synchronized with each other, as discussed later, to facilitate subsequent processing of the collected signal data.

Further, the wireless sensors according to one embodiment of the present invention can include different sensing components for monitoring a plurality of different vital signs. For example, one sensor can include a pressure detector for monitoring the pulse rate, and another sensor can include an electrochemical detector for blood glucose level measurement or the like. Thus, wireless sensors of different types for monitoring different vital signs can be conveniently worn by the subject depending on the needs of care for the subject.

The use of hybrid sensors can provide a caregiver with more comprehensive information regarding the subject's condition in a more efficient and/or more reliable manner. For example, monitoring different vital signs simultaneously using different types of wireless sensors can provide redundancy and improved robustness of monitoring quality as well as facilitate reconciliation of inconsistencies among the data gathered from different types of sensors (for different vital signs), reduce false alarm rates, etc. Certain vital signs can also be considered as having higher priorities (e.g., because the sensors for monitoring these vital signs have higher reliability or accuracy), and as such, the data gathered for these vital signs can be given more weight when data gathered for other vital signs may suggest a different condition the subject is in. In addition, when implanted wireless sensors are used, especially those implanted relatively deep within the subject's body (e.g., in the subject's heart), one or more surface attached sensors, e.g., those located near the implanted sensors, can be used to relay the signals acquired from the implanted sensors, e.g., to a master node, thereby providing potentially better quality signals for further processing and analysis while allowing for reduced power consumption of the implanted sensors. The wireless sensors can be further used in conjunction with certain medical devices worn by the subject (e.g., rehabilitating devices, robotics, prostheses, etc.), for collecting and transmitting sensed signals as a feedback or input for these devices so as to further enhance their functionalities.

The data collected from different types of sensors can be weighted, ranked, processed, validated, transmitted (via the master node, for example) to an Electronic Health Record (EHR) server, and utilized with other data in the EHR of a subject. The ECG and other vitals can be prioritized by the subject disease conditions and health status. For example, an otherwise healthy patient having atrial fibrillation (AF) surgery has a limited set of parameters, whereas a patient just discharged with Congestive Heart Failure (CHF) with co-morbidities of diabetes, and obesity, and multiple medications can be monitored for those vital sign signals relevant to disease specific algorithms based on ECG, blood glucose levels and weight.

For example, the system can store "diagnostic templates" containing threshold levels of specific vital signs, which can trigger a diagnosis when the threshold levels for the vital signs are reached by a subject undergoing monitoring. In response to subject-specific information, the system can adjust the "diagnostic templates" based on disease-specific risk factors (e.g. heart rate variability in subjects having atrial fibrillation) as well as subject-specific risk factors (e.g. fluctuation in blood pressure in subjects with hypertension). The system can also differentially weigh different vital signs according to the indication and subject's existing conditions, measure the subject's vital sign variability, trends over time, and deviations from previous states using predetermined statistical models, for example, statistical models that use measurements such as average, standard deviation, and covariance. The data processing and analysis can be performed on the sensor nodes, or by a monitoring device that is configured to receive the sensor data from the various sensors or from a master node. The monitoring device may be a device local to the subject, such as a portable electronic device (such as a cell phone, PDA, tablet, etc.), or may be remote from the subject, such as an Internet server or the like. Communications with such a remote device may be made through an intermediate device, such as a cell phone or other wireless device, that is local to the user and capable of forwarding information received from the sensor nodes to the remote server. The monitoring device may be configured, e.g., through a suitable program, to communicate with one or nodes to collect related sensor information, process this sensor information and then present, such as on a screen or by way of any other suitable user interface, information related to the collected sensor data, or to forward this sensor data, in raw or processed form, to a remote device, such as a server of a healthcare provider.

Figure 4:
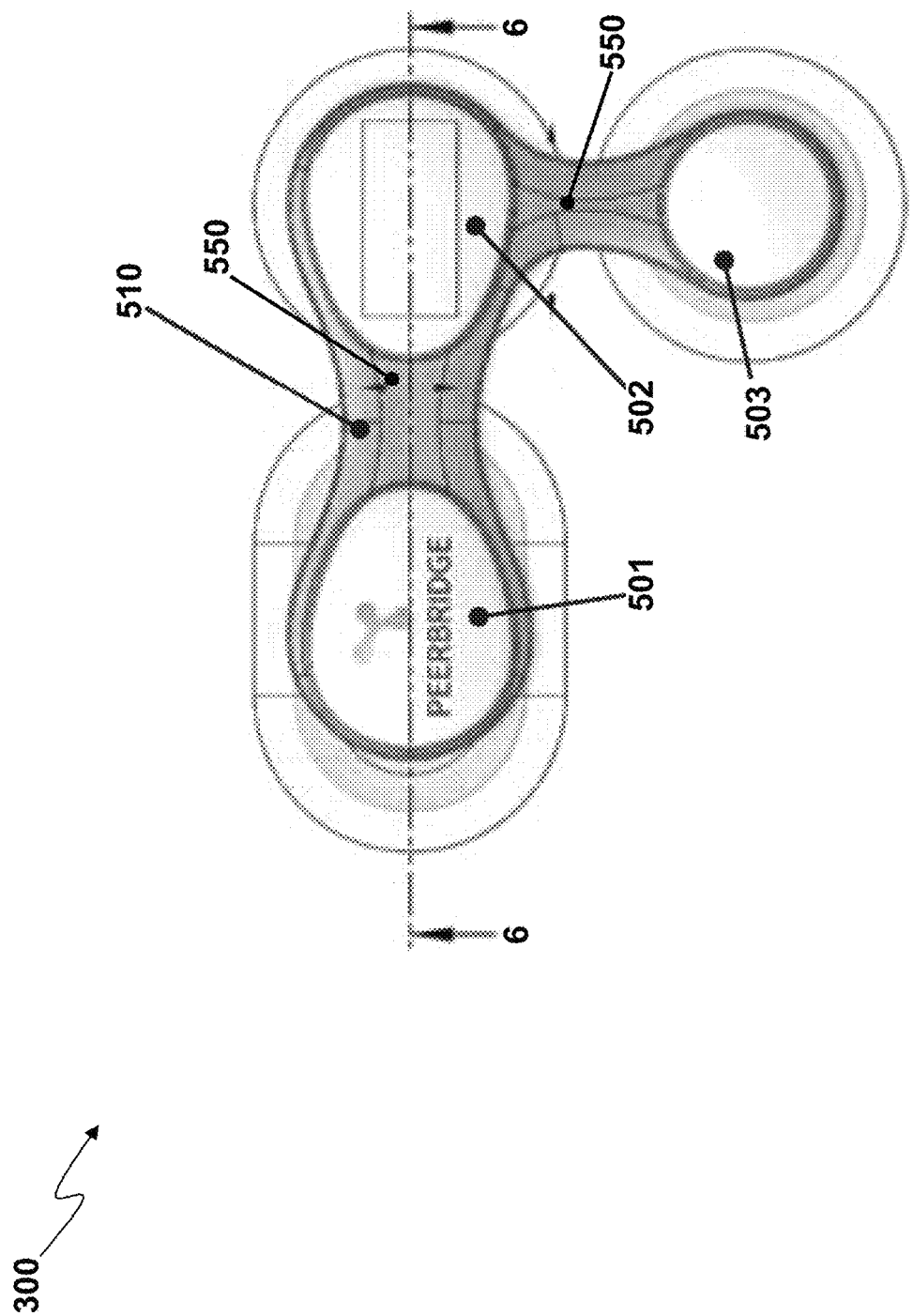
FIG. 4 is a top view of a first embodiment ECG sensor package.
Figure 5:
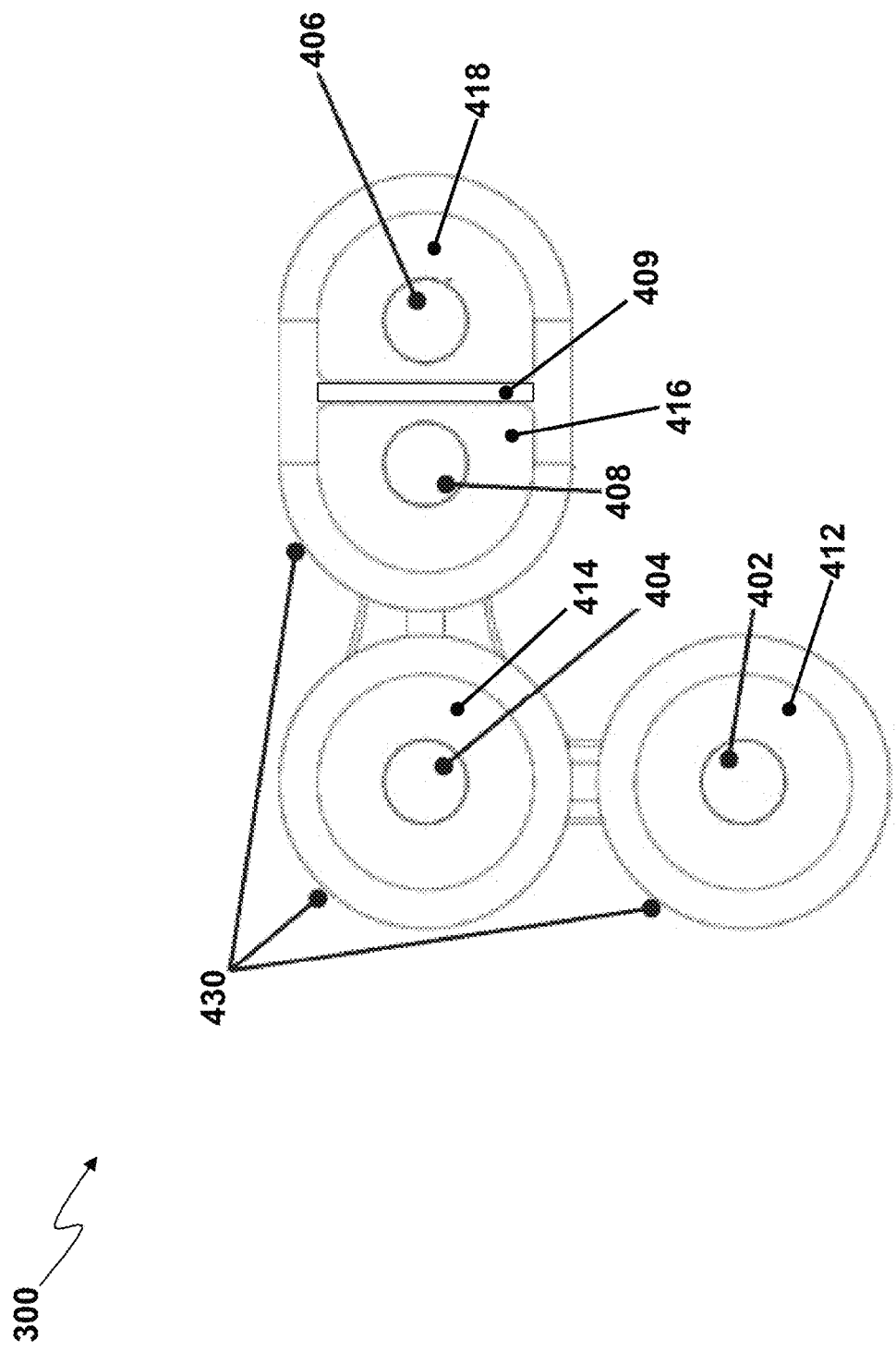
FIG. 5 is a bottom view of the sensor package shown in FIG. 4.
Figure 6:
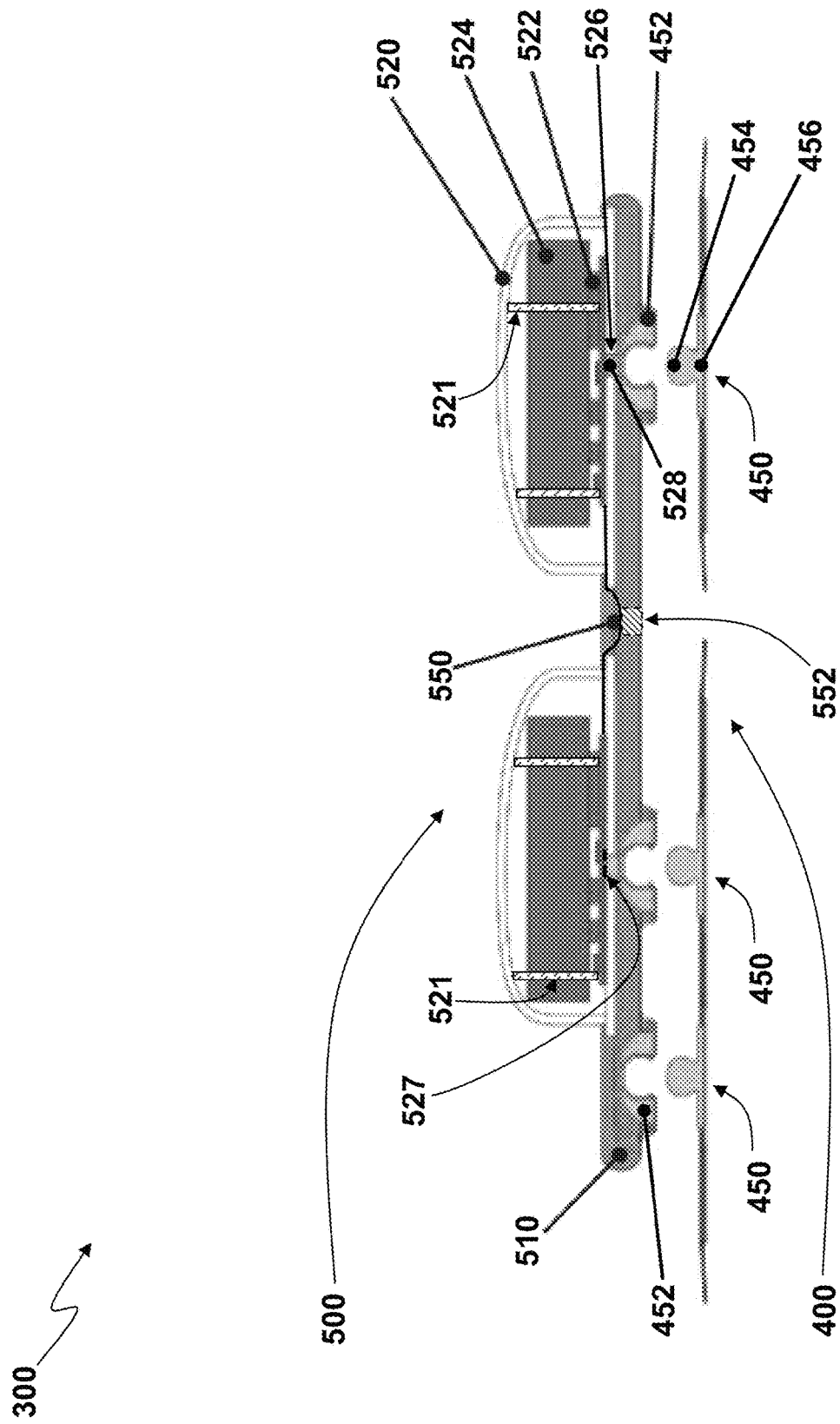
FIG. 6 is a cross-sectional view of the sensor package shown in FIG. 4 along a line 6-6.

A first embodiment first sensor package 300 is shown in FIGS. 4-6, which is used, for example, as an ECG sensor, such as the ECG sensor 200 above—although other sensing capabilities are certainly possible. The ECG sensor package 300 includes an adhesive electrode patch 400 that is removably connected to electronics package 500. In preferred embodiments, snaps 450 are used as releasable electrical connectors to both physically and electrically removably connect the adhesive electrode patch 400 to the electronics package 500. Each snap 450 includes a first part 452 on the electronic package 500, such as a female part, and a corresponding second part 454 on the adhesive electrode patch 400, such as a male part. Hence, in use, the adhesive electrode patch 400 is first preferably placed at the desired location on the subject, where it adheres to, and makes electrical contact with, the subject's skin. Then, the electronics package 500 is snapped onto the adhesive electrode patch 400 via the snaps 450, to mechanically and electrically connect the electronics package to the adhesive electrode patch 400. It will be appreciated that other types of releasable electrical connectors could be used, such as a plug-and-socket arrangement, a magnetic-connector arrangement, or the like, as known in the art, each formed by a first part that can releasably connect to a second part to establish an electrical connection.

As illustrated in FIG. 5, the adhesive electrode patch 400 includes three ECG electrodes 402, 404, 406 arranged in an L-shaped configuration with respect to each other, and a single ground electrode 408 adjacent to one of the ECG electrodes 406 along one of the arms of the L-shaped configuration. It will be appreciated that the electronic ground electrode 408 may be disposed anywhere on the device 300 so long as it is electrically connected to both the subject and the electronics package 500. In preferred embodiments, the distance between electrodes 402, 404, 406 is approximately two inches in both the horizontal and vertical directions. In other embodiments, the horizontal and vertical distances between electrodes 402, 404, 406 is less than two inches, such as 1.5 inches or one inch, or even one inch or less, depending upon the capabilities of the analog front end 299. It will be appreciated that in other embodiments the distances between the electrodes 402, 404, 406 can be greater than two inches, with the distance limited only by the physical extents of the user. Adhesive electrode patch 400 maintains the orientation and spacing between the electrodes 402, 404, 406 substantially fixed, and knowledge of this predetermined spacing and geometrical arrangement of the electrodes 402, 404, 406 can be used in subsequent signal processing to obtain or compute additional channels of ECG data.

The electrodes 402-408 are preferably formed from an electrically conductive hydrogel material, such as KM30B from Katecho, Inc., of Des Moines, IA A foam barrier 409, preferably a closed-cell foam such as Katecho SP 275, is used to help electrically isolate the ground electrode 408 from its neighboring ECG electrode 406. Each electrode 402-408 is surrounded by a respective hydrocolloid layer 412-418, which also adheres to the skin of the subject. A suitable hydrocolloid material includes, for example, Hi-Tack Hydrocolloid from Amparo, Inc., of Placentia, CA Finally, a protective layer 430 surrounds the hydrocolloid layers 412-418 and also adheres to the skin of the subject. Each electrode 402-408 is electrically connected to a corresponding and respective second snap part 454; in preferred embodiments, the top surface of each electrode 402-408 directly contacts a bottom portion 456 of the corresponding second snap part 454.

As illustrated in FIGS. 4 and 6, the electronics package 500 includes a flexible substrate 510 to which are bonded three, separate compartments 501, 502, 503. Pairs of the compartments 501-503 are electrically connected to each other by way of respective flexible circuits 550. In preferred embodiments, the flexible circuits are flexible circuits boards. It will be appreciated, however, that flexible wires may also be used for the flexible circuits 550, without the need for a flexible circuit board. The flexible substrate 510 is preferably made from a resilient, electrically insulating material, such as silicone rubber or an elastic textile. By way of example, the flexible substrate 510 may be molded from PolyOne thermoplastic elastomer (TPE), of Avon Lake, OH. The flexible circuit boards 550 are U-shaped between their respective pairs of compartments 501-503 and are preferably disposed within the substrate 510. For example, the flexible circuit boards 550 may be molded into the substrate 510, and during this molding process a tool of the mold may form a respective depression in each of the flexible circuit boards 550 which forms the U-shaped depression or bulge around which the substrate 510 is molded. The U-shape of each flexible circuit board 550 provides for greater resilience and stretching of the flexible circuit boards 550 between the compartments 501-503. Collectively, the compartments 501-503 provide the electronics corresponding to, for example, the logic indicated in FIG. 2. It will be appreciated that other strain-relief features may be used for the circuit boards 550, such as a zig-zagging pattern across the surface of the substrate 510, or the like. Fundamentally, the length of each flexible circuit board 550 is preferably substantially longer than the distance between the compartments 501, 502, 503 between which it is connected, so as to allow for some latitude of stretching and thus strain relief Additionally, in certain embodiments, the substrate 510 may be formed so that a portion of one or more of the flexible circuit boards 550 is exposed from substrate 510, forming a contact region 552 for the flexible circuit board 550. This contact region 552 can include exposed electrical contacts on the flexible circuit board 550. These exposed electrical contacts can be used to electrically connect with the electronics of the sensor package 300, for example to provide for charging of the battery or batteries 524 and for use as data input/output (I/O) with an external device, such as to obtain data stored in the sensor 300, to provide data to the sensor 300, to program the sensor 300, etc.

Each compartment 501-503 is disposed over a respective snap 450 and is defined by a rigid shell 520, and thus an overall L-shaped structure is formed by the electronics package 500 corresponding to the L-shaped layout of the ECG electrodes 402-406. Each shell 520 may be made, for example, from plastic or any other suitable material, and is preferably water-resistant. In particular, each shell 501-503 is preferably over-molded with the substrate 510 so that any seams between the bottom surface of the shell 501-503 and its top cover are covered by and sealed with the substrate 510. Any suitable material may be used for the shells 501-503, such as plastic, polycarbonate or the like. By way of example, SABIC Lexan HPl may be used, of Pittsfield, MA Each shell 520 is used to house and protect corresponding sub-system electronics 522 (and related PCB, if required), batteries 524 or both. Collectively, the subsystem electronics 522 in the shells 520 form the electronics of the package 500, which monitor sensor signals arriving from the electrode patch 400 and transmit corresponding physiological data to another device, such as a master node. In preferred embodiments, the batteries 524 are free-floating within their respective shells 520 to accommodate any swelling of the battery 524, as well as mechanical tolerances. The flexible circuit boards 550 are used to exchange power, signals or both between the compartments 501-503, and can include, for example, the open leads discussed above in reference to ECG sensor system 200 to ensure superior signal acquisition and noise rejection. The flexible circuit boards 550 are preferably sealed to each shell 520 that the circuit board 550 enters so that stress on the flexible circuit board 550 is not transferred to the electronics or PCB 522 within the shell 520. For example, an over-molding process may be used to form the compartments 501-503 while simultaneously sealing the flexible circuit boards 550 with the compartments 501-503; or, the top cover of each compartment 501-503 may be bonded (by gluing, ultrasonic welding, over-molding, etc.) to the bottom surface of the compartment 501-503 while simultaneously sandwiching the flexible circuit board 550 therebetween. The resultant structure formed by the interconnected compartments 501-503 and flexible circuit boards 550 may then be used in another or same over-molding process that is used to form the substrate 510.

Each shell 520 also includes an opening 526 through which is disposed a conductor 528 to establish an electrical connection between the first snap part 452 and the subsystems electronics 522 within the shell 520. The conductor 528 may be embedded in its respective shell 520 in the over-molding process that creates, for example, the floor of the compartment 501-503, while the first snap part 452 may be embedded in the substrate 510 in the over-molding process that is used to form the substrate 510. The conductor 528 preferably seals the opening 526 to ensure that the shell 520 remains water-resistant. Further, because the bottom surface of the shell 520 may bend and thus suffer vertical displacements with respect to the PCB 522, in preferred embodiments the PCB 522 is not rigidly connected to the conductor 528 but is instead flexibly electrically connected to conductor 528, such as by way of a metallic spring 527 or the like; the PCB 522 may mechanically engage with pins 521 within its respective shell 520 to, for example, avoid lateral displacements and/or to push the PCB 522 towards the spring 527. Hence, the conduction paths of ECG and ground signals from the subject may flow as follows: (1) skin of the subject, (2) hydrogel electrode 402-408, (3) second snap part 454, (4) first snap part 452, (5) conductor 528, spring finger 527 and finally (6) PCB and related sub-system electronics 522 within the shell 520.

Dividing the electronics of the sensor 300 into the multiple compartments 501-503 has various advantages. For example, because of the flexible nature of the substrate 510, as well as the U-shaped interconnecting circuit boards 550, a great deal of elasticity and flexibility is provided between the compartments 501-503. The elasticity and flexibility allow sensor 300 to exhibit limited deformation in multiple dimensions. The limited deformation provides strain relieve and lessens the tug on any adhesive discussed below, which in turn will improve the longevity of the adhesion on the body. Moreover, the electronics 522 can be separated and modularized based upon function so as to reduce crosstalk, electrical interference or both within the sensor package 300. In particular, it is desirable that the wireless transceiver electronics be spaced from the analog front end 299 of the signal collection circuitry, and in particular from the analog-to-digital (AID) circuits. Hence, in preferred embodiments, the wireless transceiver is disposed within one compartment 501 at the end of one leg of the L-shaped structure, while the AID circuits and related analog front end circuitry 299 are placed in the compartment 503 at the end of the other leg of the L-shaped structure. The central compartment 502 at the juncture of the legs of the L-shaped structure could contain, for example, the digital processing equipment, including a microprocessing unit, memory (volatile, non-volatile or both) and the program code stored in the memory and executable by the microprocessing unit to control operations of the sensor package 300. Suitable traces are provided on the flexible circuit boards 550 to deliver ECG and ground signals from the respective electrodes 402-408 to the analog front end 299 in compartment 503, to support noise rejection, and to also carry power and digital signals between the compartments 501-503.

Figure 7:
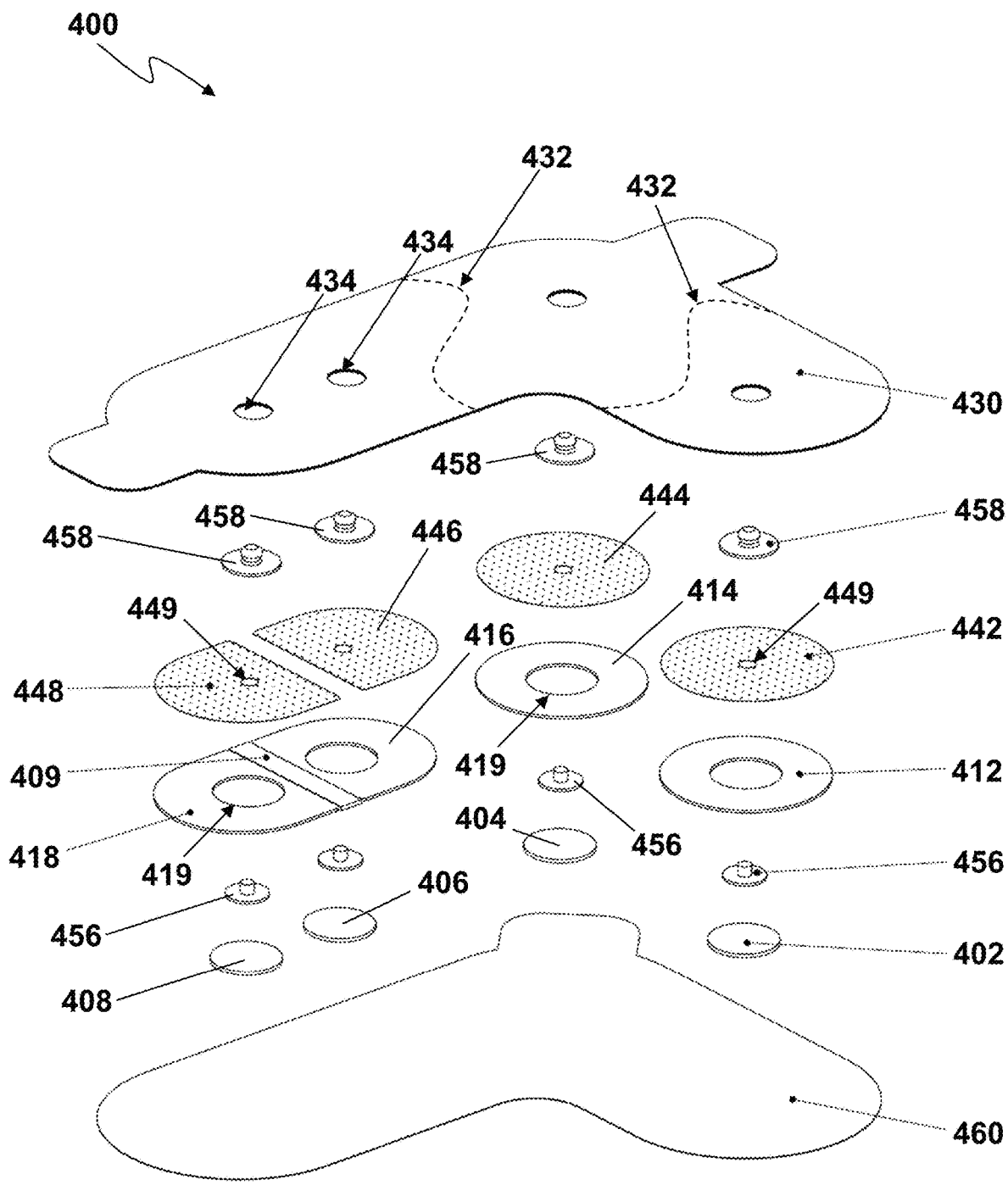
FIG. 7 is an exploded perspective view of an adhesive electrode patch depicted in FIG. 6.

FIG. 7 shows an exploded view of an embodiment of the adhesive electrode patch 400. As indicated in FIG. 7, the adhesive electrode patch 400 is a layered structure formed from multiple subcomponents. A single protective layer 430 forms the top-most layer of the structure 400, covering and extending beyond all other layers, and serves to protect the layers below it from water, oils, soap and other materials. Any suitable material may be used for the protective layer 430. For example, the protective layer 430 may be made from polyurethane that is about 2.5 mils thick. The protective layer is preferably breathable, however, with a moisture vapor transmission rate (MVTR) of, for example, between 300 to 1400 gm/m2/day. The bottom surface of protective layer 430 preferably includes an adhesive, such as an acrylic adhesive, which is used to bind to both the layers immediately underneath it and to the skin of the subject, thus forming a water-resistant seal around the adhesive electrode patch 400. The protective layer 430 includes openings 434 that each correspond to a respective electrode 402-408.

The second part 454 of each snap 450 is formed from two subcomponents, including a top component 458 and a bottom component 456. Each top component 458 provides the male part of snap 450 extending from a respective flange, and may be coated, for example, with silver and silver chloride, and which is disposed through a respective one of the openings 434 in the protective layer 430. The top surface of the flange on the top component 458 preferably adheres to the adhesive on the bottom surface of protective layer 430. The bottom component 456 of each second snap part 454 includes a stud extending from a respective flange, with the stud mating with the corresponding top component 458.

Below the top component 458 of each snap 450 is a separate, respective backer 442, 444, 446, 448. Each backer 442-448 is used to provide mechanical strength to the respective electrode 402-408, and in particular to prevent the respective second snap part 454 from pulling out of the adhesive electrode patch 400 when under tension. Any suitable material may be used for the backer 442-448, such as polyethylene terephthalate (PET). The backer 442-448 is preferably breathable; perforated PET may be used, for example, for this purpose. Each backer 442-448 includes an opening 449 that is sized to accept the stud of bottom component 456 of the respective second snap part 454 but not the corresponding flange. Each backer 442-448 is thus sandwiched between the flanges of the top component 458 and bottom component 456 of each second snap part 454. The remainder of the top surface of each backer 442-448 adheres to the bottom surface of the protective layer 430.

The hydrocolloid layers 412-418 are individually disposed underneath the respective backers 442-448, with the foam barrier 409 being disposed between hydrocolloid layer 418 and hydrocolloid layer 416, as previously described, so as to better electrically isolate ground electrode 408 from ECG electrode 406. The natural adhesive properties of the hydrocolloid layers 412-418 causes their top surfaces to adhere to the corresponding backer 442-448 and their bottom surfaces to adhere to the skin of the subject. However, additional adhesives can be used if desired. The top and bottom surfaces of the foam barrier 409 are preferably coated with an adhesive, such as an acrylic adhesive, to respectively adhere to the bottom surface of protective layer 430 and the skin of the subject. Each hydrocolloid layer 412-418 includes an opening 419 sized to accept the flange on of the bottom component 456 of the respective second snap part 454 as well as the respective electrode 402-408, which lies under its respective bottom component 456 of the second snap part 454. Hence, the bottom component 456 is sandwiched between its respective backer 442-448 and its respective electrode 402-408, with the bottom of the bottom component 456 contacting, and thus electrically coupling to, its respective electrode 402-408. Additionally, each electrode 402-408 thus lies within the respective opening 419 in its respective hydrocolloid layer 412-418. Like the hydrocolloid layers 412-418, the natural adhesive properties of the hydrogel electrodes 402-408 causes their top surfaces to adhere to both the corresponding backer 442, 448 and the flange of bottom portion 456 of the corresponding second snap part 454, while the bottom surface of each electrode 402-408 adheres to the skin of the subject.

In preferred embodiments, the protective layer 430 includes perforations 432. The perforations 432 define areas respectively corresponding to each compartment 501-503, and are designed to tear when placed under excessive stress.

Hence, due both to the frangible nature of protective layer 430, as well as the flexibility and stretching capabilities of the substrate 510 and circuit boards 550, the sensor package 300 is capable of accommodating a wide variety of motions of the subject without pulling away from the skin, and thus ensures solid and reliable electrical connections between the electrodes 402-408 and the skin of the subject.

Figure 8:
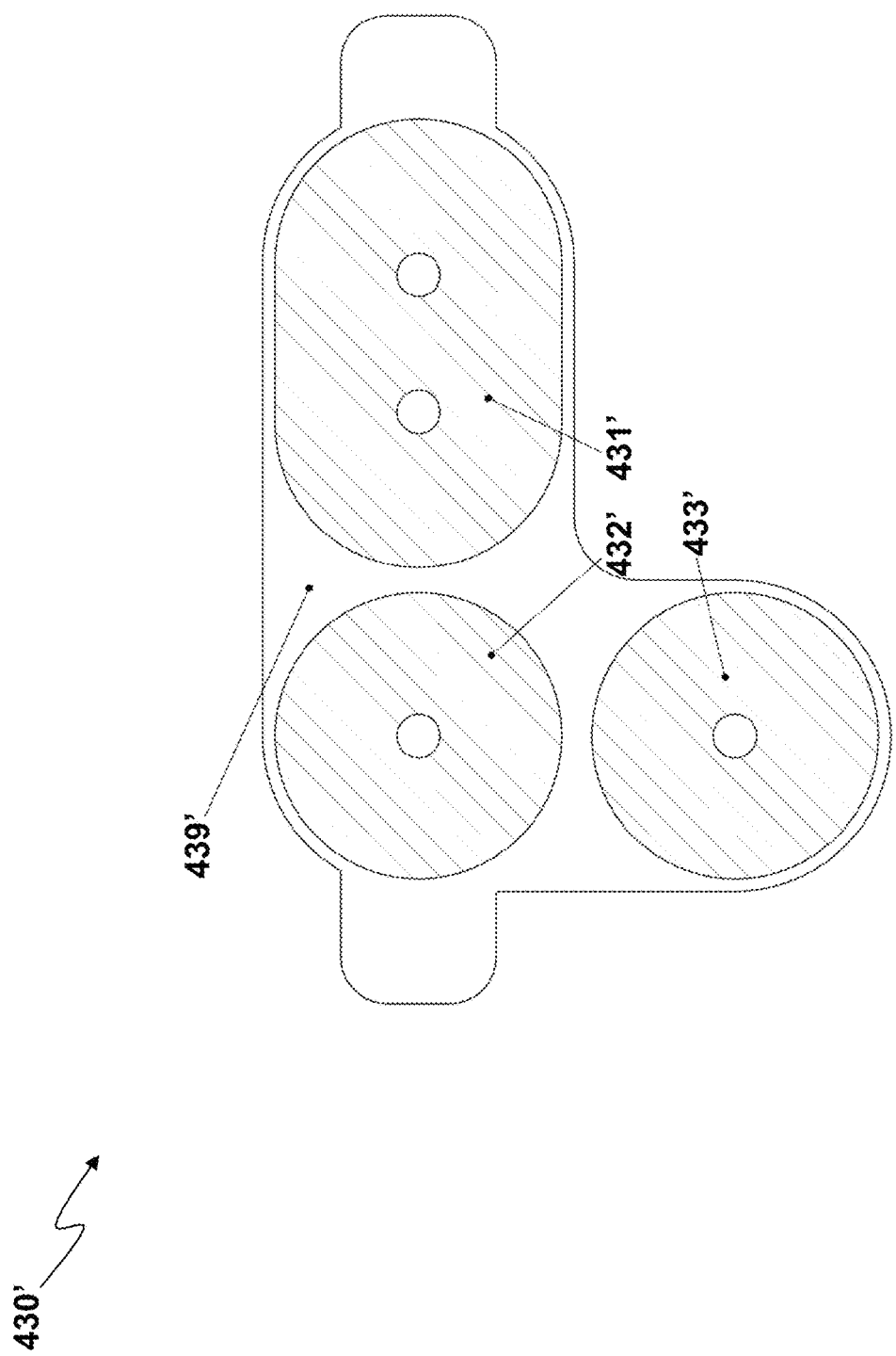
FIG. 8 depicts another embodiment of a protective layer shown in FIG. 7.
Figure 9:
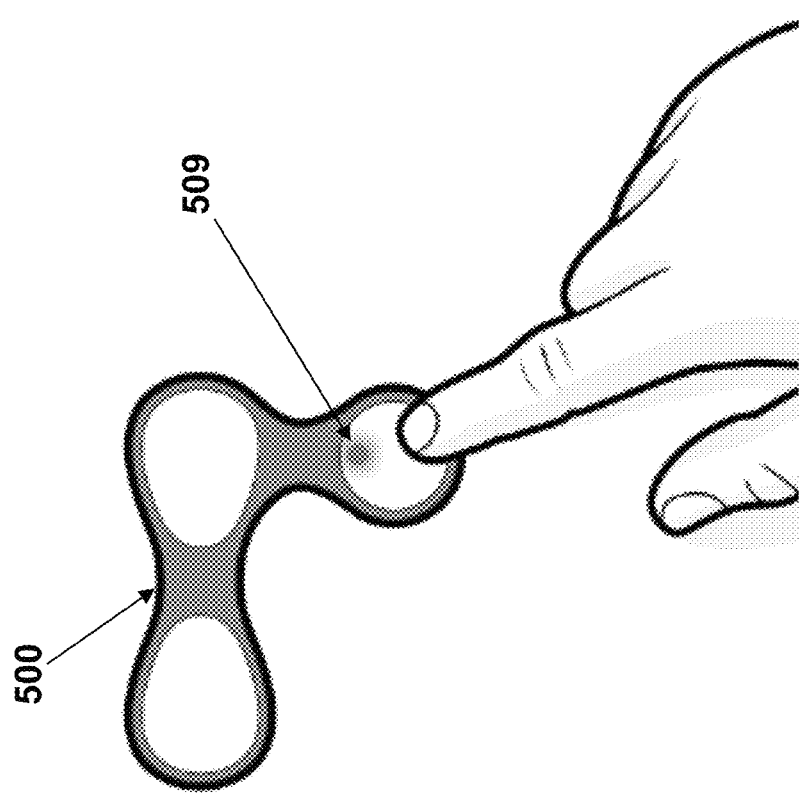
FIGS. 9-12 depict steps that may be employed to attach the adhesive electrode patch depicted in FIG. 6 to a subject.

In other embodiments, as shown in FIG. 8, rather than providing a single protective layer 430 with built-in stress relief via perforations 432, a protective layer 430' may instead be formed as three separate layers 431'-433' adjacent to each other, each corresponding to a region of a respective compartment 501-503. In such embodiments, it may be desirable to include a single release liner 439' disposed over the top surfaces of the three, separate protective layers 431'-433' so as to keep them in proper geometrical alignment with each other; once the electrode patch is attached to the skin of the subject, this top release liner 439' can then be peeled away, leaving the three separate protective layers 431'-433' exposed.

Finally, referring back to FIG. 7, a bottom release liner 460 is provided, which is used to protect the bottom surface of adhesive electrode patch 400, such as the bottom surfaces of the electrodes 402-408, the hydrocolloid layers 412-418, and the protective layer 430 or layers 431'-433'. The bottom release liner 460 is peeled away from the bottom surface of adhesive electrode patch 400 prior to application of adhesive electrode patch 400 to the skin of the subject. As indicated above, a release liner may also be provided for the top surface of the adhesive electrode patch 400, and which is removed prior to attaching the electronics package 500 to the adhesive electrode patch 400.

FIGS. 9-12 illustrate embodiment steps that may be employed to use the sensor package 300. Prior to applying the adhesive electrode patch 400, the user or medical practitioner may first turn on the electronics package 500 to verify that it establishes wireless communications with the master node. For example, one of the compartments 501-503 of the electronics package 500 may include a button which, when pressed, turns on the electronics package 500. Hence, in certain embodiments, the top surface of the compartment 503 may be flexible so that it returnably deforms under suitable pressure from the user to, in turn, press on a switch disposed within the compartment 501-503. Preferably, the switch, when activated, provides both tactile and audible feedback of being depressed. Upon activation by this switch, the electronics package 500 begins looking for a master node to synchronize with, and this initial synchronization step may be indicated by the flashing of an LED interface 509. Success or failure of this synchronization may be indicated by way of this LED interface 509.

Once the electronics package 500 is verified as working properly and capable of synchronizing with the master node, the adhesive electrode patch 400 may then be applied to the subject. The top surface of the electrode patch 400, such as the protective layer 430 or a release liner, may have markings or indicia used to indicate a centerline 401 that is to be aligned with the centerline of the chest of the subject. The top edge of the adhesive electrode patch 400 is then further aligned about 1 inch below the heads of the collar bone. The location of the adhesive electrode patch 400 on the subject is then noted for subsequent preparation of this region for application of the adhesive electrode patch 400, in which the region is shaved (if needed), abraded according to skin condition and then cleaned with alcohol wipes.

Figure 10:
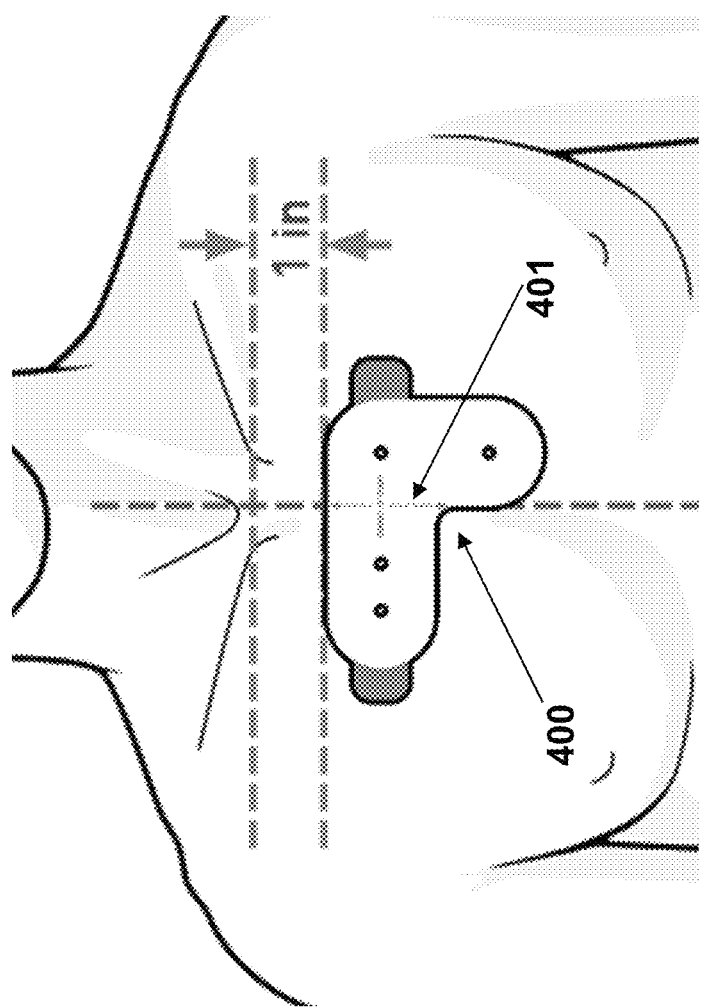
Figure 11:
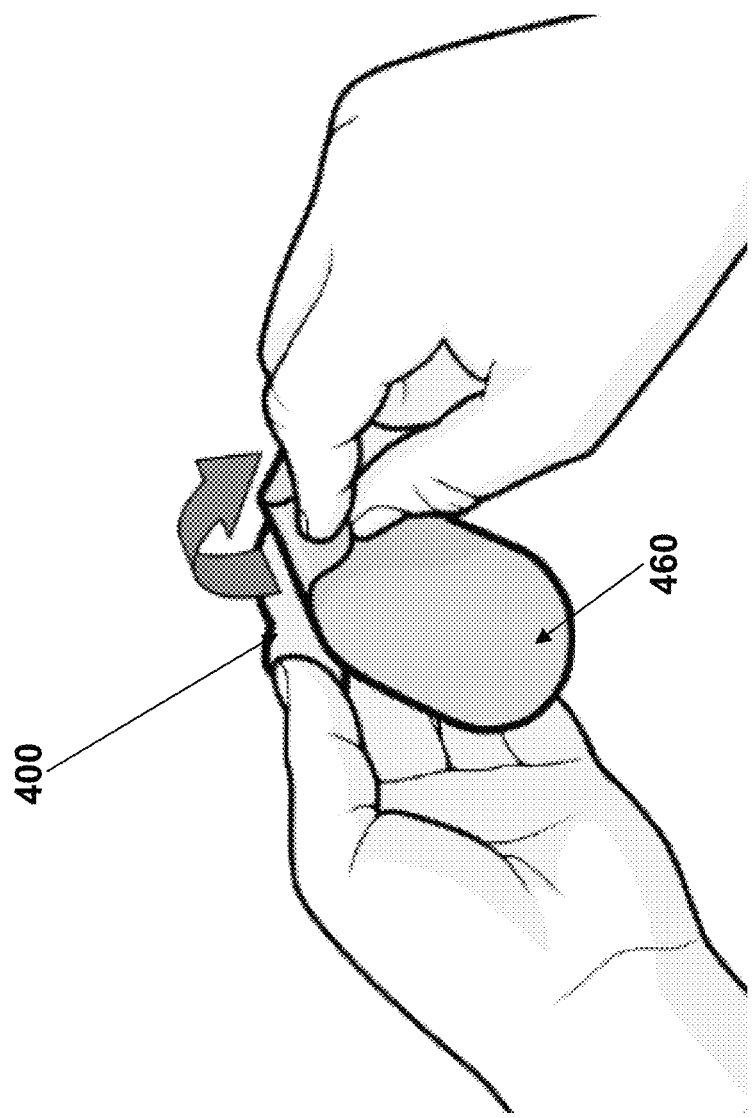
Figure 12:
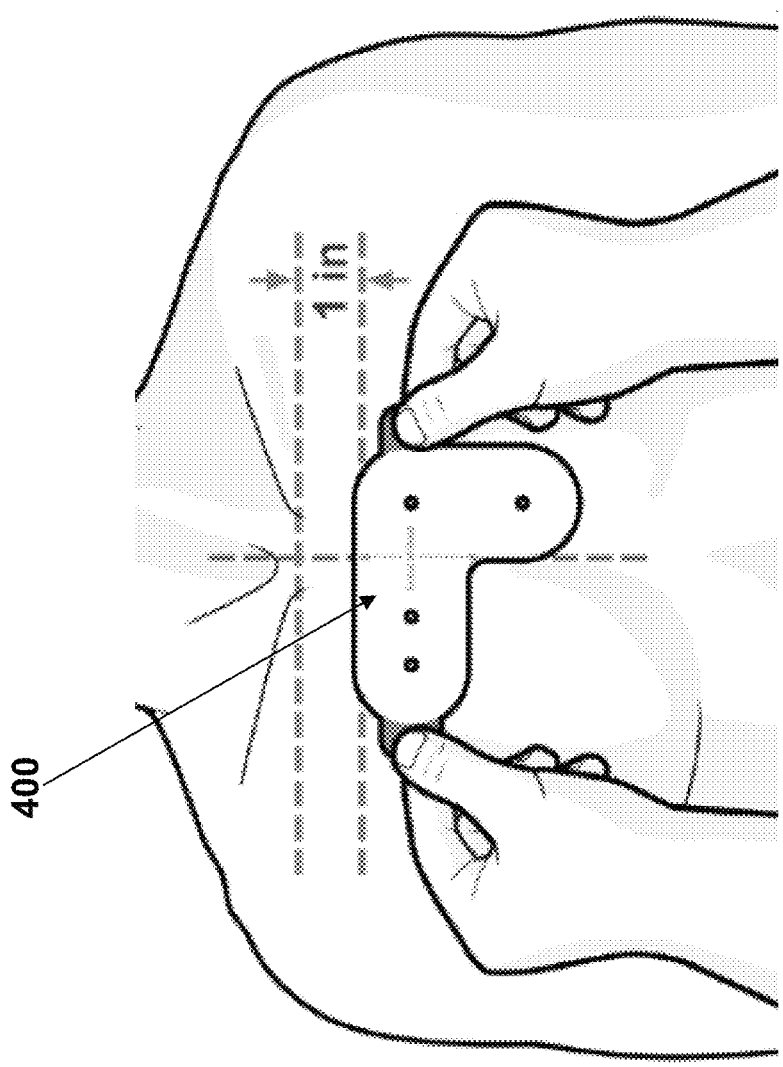

Then, as shown in FIGS. 11 and 12, the release liner 460 is removed from the back of adhesive electrode patch 400 and the adhesive electrode patch 400 is applied to the prepared region of the skin at the location previously determined in FIG. 10 and secured into position by pressing firmly around the perimeter of the electrode patch 400. Thereafter, the electronics package 500 may be coupled, via the snaps 450, to the adhesive electrode patch 400.

Figure 13:
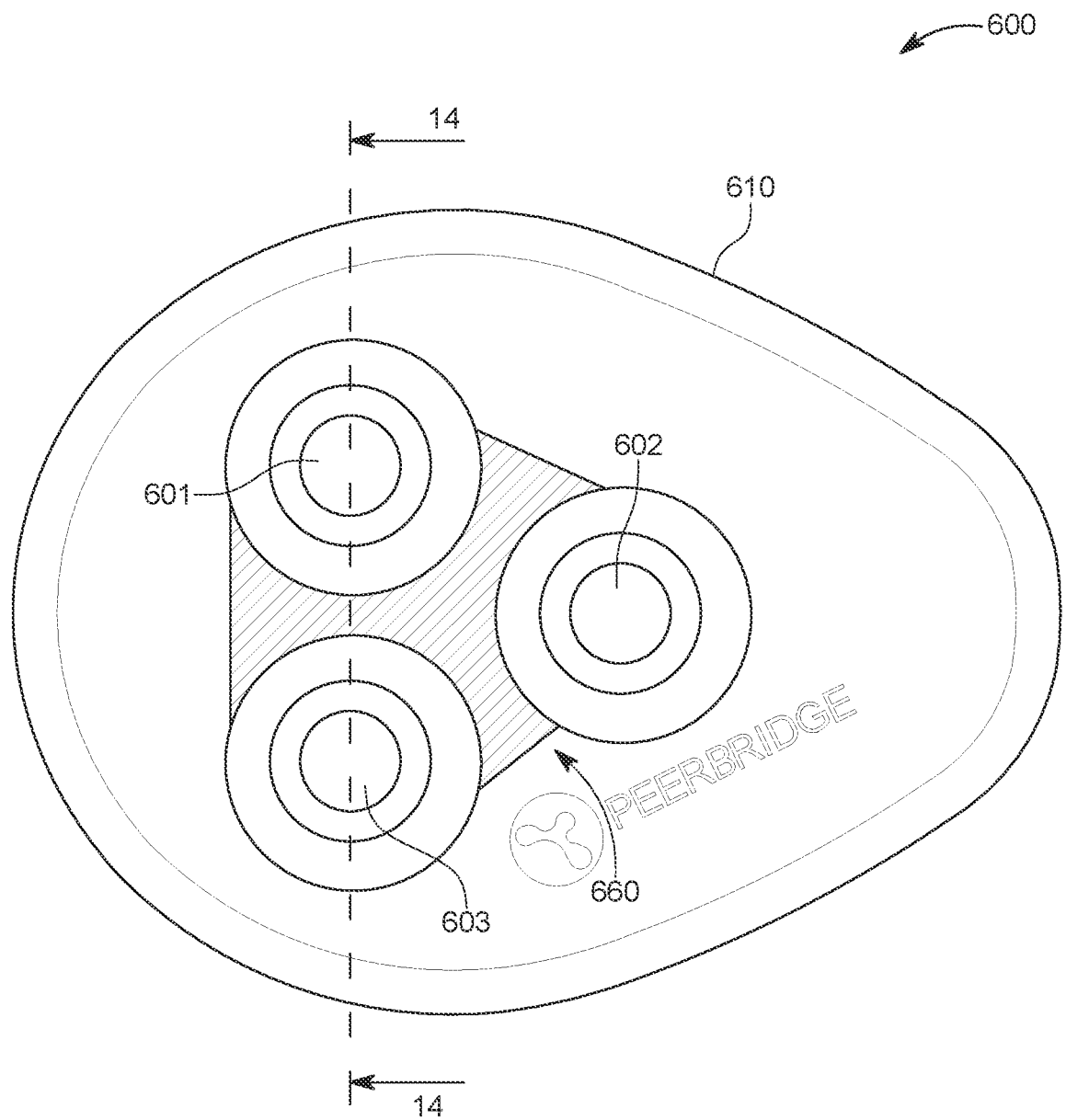
FIG. 13 is a bottom view of another embodiment sensor package.
Figure 14:
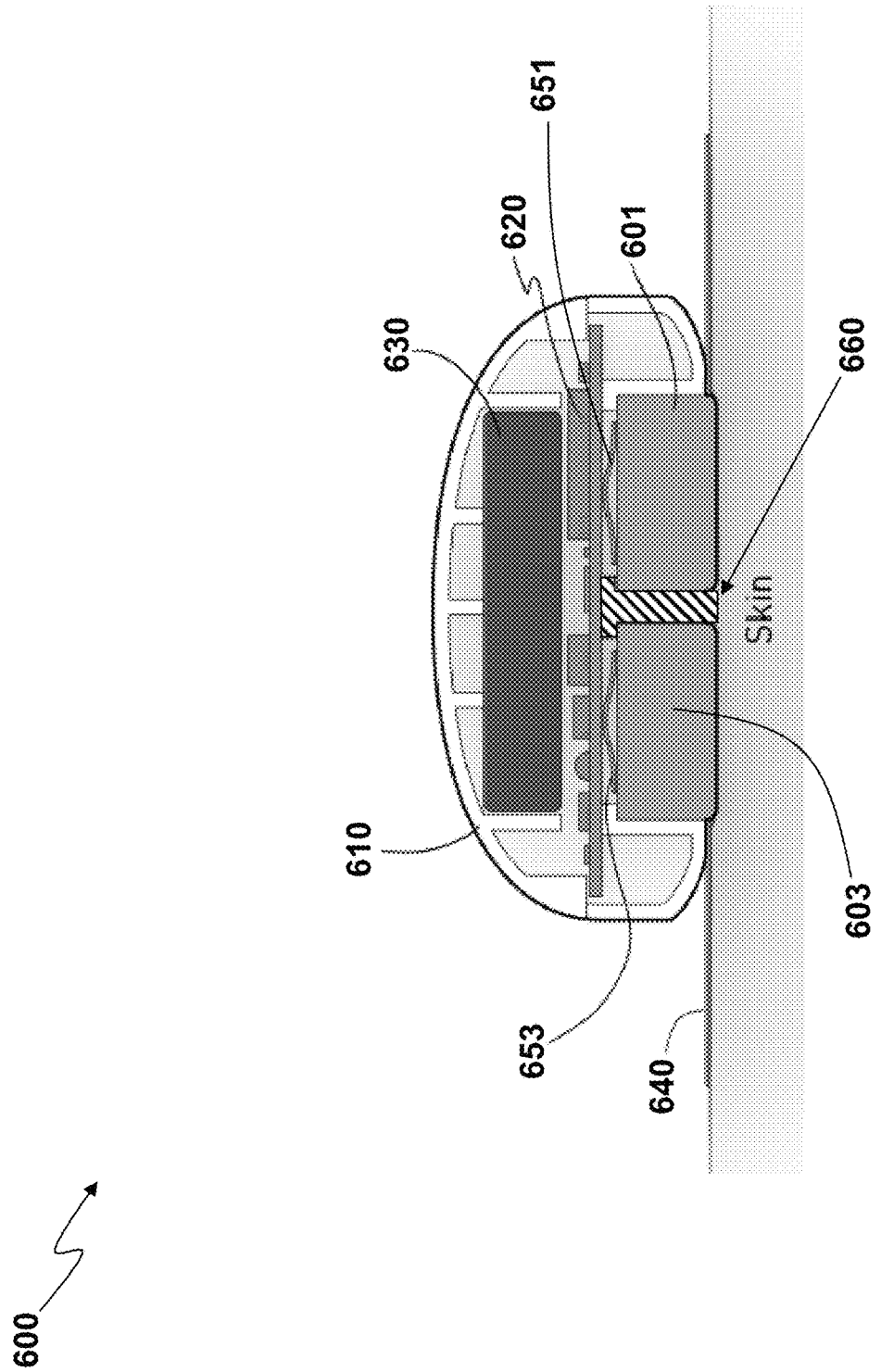
FIG. 14 is a cross-sectional view of the sensor package of FIG. 13 along line 14-14.

FIGS. 13 and 14 illustrate a second embodiment sensor package 600. The sensor package 600 includes, for example, three sensors 601-603, which may be any type of sensor, including sensors based upon electrical characteristics, optical characteristics, thermal characteristics, chemical characteristics, or the like. By way of example, the first sensor 601 may be a skin temperature sensor, the second sensor 602 may be a sweat and/or hydration sensor and the third sensor 603 may be a blood oxygen sensor. The sensor package 600 includes a shell 610 within which are disposed the sensors 601-603, as well as electronics 620 (and related PCB) coupled to both the sensors 601-603 and to a battery 630. The shell 610 is preferably made from a rigid material to protect the electronics 620 and battery 630, and may be made from any suitable material, such as plastic. The shell 610 includes one or more openings through which the sensors 601-603 extend to contact the skin of the subject. The sensors 601-603 are preferably sealed with the shell 610, each other, or both to prevent the ingress of water or other contaminants into the interior cavity of shell 610. Alternatively, or additionally, the sensors may be configured to be replaceably disposed within the shell 610 so that different types of sensors may be swapped in and out depending upon, for example, the desired physiological condition to be measured, exhaustion of the sensor, etc. An adhesive substrate 640 is coupled to the shell 610 and is used to secure the sensor package 600 to the skin of the subject. As in the previous embodiment sensor 300, the adhesive substrate may be removably connected to the shell 610.

Preferably, each sensor 601-603 is moveably disposed with respect to the shell 610 and includes a respective biasing element 651-653 that is used to push or bias the sensor 601-603 towards the skin of the subject. The biasing element 651-653 may be, for example, a spring, a layer of foam, or the like. In specific embodiments, based upon the type of sensor 601-603 used, the biasing element 651-653 may be a spring contact that is also used to establish an electrical connection between the sensor 601-603 and the electronics 620. Additionally, foam 660, such as a closed-cell foam, may be used to electrically and optically isolate the sensors 601-603 from each other. The bottom surface of the foam 660, which contacts the skin of the subject, may be provided with an adhesive layer to adhere to the skin surface.

Figure 15:
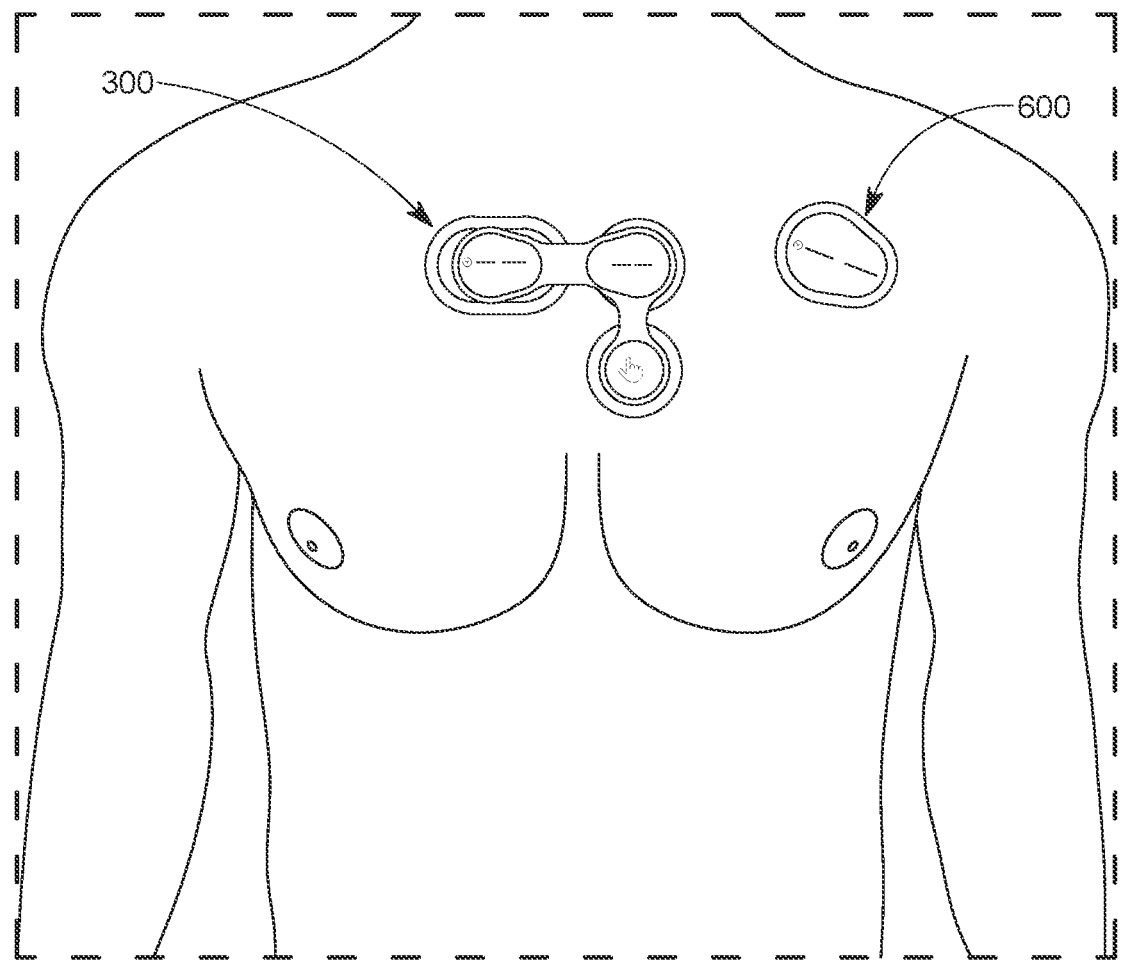
FIG. 15 illustrates usage of the sensor package of FIG. 4 in combination with the sensor package of FIG. 13.

As illustrated in FIG. 15, by way of example, the sensor packages 300, 600 may be deployed together to monitor various aspects of the subject, including the gathering of ECG data via first sensor package 300 and the collection of subject temperature, blood oxygen levels and hydration levels or ionic balance via second sensor package 600. By way of further example, one of the sensor packages, such as the first sensor package 300, can be designated as a master node. The second sensor package 600 can establish a wireless connection with the first sensor package 300 as the master node to relay subject temperature, blood oxygen and hydration information to the first sensor package 300, as well as to synchronize with the first sensor package 300. The first sensor package 300, as the master node, can then forward this received information to a local monitoring device, such as a subject's cell phone, tablet, laptop computer, desktop computer, or any other suitable device, including a remote device via cellular or satellite communications. The local monitoring device may process the collective sensor data received from the first sensor package 300 and provide corresponding medical information to the subject, a healthcare provider, a remote server or the like. Alternatively, each sensor package 300, 600 may directly communicate and synchronize with the local monitoring device to send sensor data directly to the local monitoring device.

Devices for the continuous monitoring of subjects require the ability to secure the related sensor components onto the desirable site for a specific duration. However, the human body surface is a dynamic environment constantly exposed to various physical and biological variables, such as movement, sweat, etc. Heterogeneity in body shape poses additional challenges when designing on-body sensors. The various embodiments of sensor packages according to the present invention, such as the sensor packages 300, 600 discussed above, provide a combination of features that allow on-body devices to stay on the skin, even on difficult topographies, for extended periods of time.

By way of example, one challenge to convention sensor systems is accommodating different body contours. For sensors that have to be placed in a specific location, such as the middle of the chest, the device should conform to the various topographies arising from differences, such as gender and body shape, or modifications of the body surface such as from disease state, previous medical/non-medical procedures, etc. For sensors that can be applied to multiple locations on the body surface, the design of the device should be able to conform to the different topographies of the various locations. By disposing the electronic components into multiple compartments 501-503, embodiments reduce the footprint of each rigid compartment 501-503 and allow the compartments 501-503 to be connected with flexible material in ways and shapes that can be tailored to the location of the device 300 placement. These features increase the range of body contours that the embodiments could be applied. Also, since the compartments 501-503 are connected to each other via flexible materials (including the flexible circuit boards 550 and the substrate 510), an overall increase in the flexibility of the device 300 is obtained, while allowing the flexibility of the device 300 to be adjusted by choosing materials with different physical properties. Further, built-in stress relief, such as is provided by the snaps 450 and the perforations 432, allows the device 300 to flex while maintaining electrical/sensor contact and increasing the range of topographies the device 300 can accommodate.

Another challenge for sensors is the size of the footprint of the device. The footprint of a device is determined by a number of factors, including the size of the sensor(s), the footprint of accessory components (e.g. battery, memory, supporting electronics) and industrial design. However, real estate on the body surface of the subject is not unlimited, such as the middle of the chest where the contour is relatively flat. The constrains of the body surface restrict the size and placement of such devices. Usability and user comfort add additional limitations to the footprint of sensor devices. The embodiment devices 300, 600 address this challenge by providing a short distance (e.g., 2 inches or less) between certain types of sensors, such as between vertical and horizontal pairs of the ECG electrodes 402-406, which reduces the footprint of the devices 300, 600 while still being able to provide clinical-grade information. Additionally, by providing separate sensor packages, such as the ECG package 300 and the supplementary sensor package 600, physical connectors between these packages 300, 600 are eliminated, thus reducing the footprint of the sensor system, which would otherwise experience difficulties on smaller bodies if these sensor systems were integrated together as a single sensor device. In support of this feature, each device 300, 600 supports wireless communications for data transfer, thus eliminating the need for wires and other physical connections. The devices 300, 600 also support wireless synchronization between themselves and/or another device to ensure data integrity when collecting sensor information across multiple nodes, especially for measurements that require high fidelity, such as ECG measurements. Additionally, the flexibility of sensor placement is increased because each sensor package 300, 600 is smaller than would otherwise be the case in a single, integrated system.

A third challenge for on-body monitoring is to accommodate various motions that the sensors will experience. These motions are generated by the movement of the entire body or specific parts of the body (such as breasts in women and body tissue in larger subjects), as well as during various activities (such as walking and climbing stairs). The ability to handle motions has a direct impact on the quality of sensors signals that are acquired as well as the longevity of the device on the body. Embodiments of the invention, such as sensor package 300, address this challenge by disposing the electronic components into multiple, separate compartments, which allow allocation and distribution of weight to specific parts of the device on the body, and which increase the flexibility of the device 300 to enhance comfort during motion. For example, for the tripole ECG sensor package 300, the heavier components, such as batteries, can be allocated to the upper two compartments 501, 502 in the middle of the chest, while the lighter components can be allocated to the bottom compartment 503 that will experience more motion because it is located near the breast area in women. Additionally, as the compartments 501-503 are connected via flexible material (including the flexible circuits 550 and substrate 510), tension and tugging during motion can be dampened within the device 300 such that the sensors 402-408 remain in good contact with the skin. Built-in stress relief, such as the use of snaps 450, perforations 432, and the separation of the sensors 402-408 into mechanically frangible or unconnected regions, allows the device 300 to flex while maintaining electrical/sensor contact, and increases the range of motion the device 300 can accommodate. Also, the use of separate compartments 501-503 allows the overall shape of the device 300 to be tailored for the strategic placement of adhesives. In particular, it is noted that adhesives come with various properties (e.g. tensile strength, and peel strength), and stronger materials are preferably shaped and placed along the angle of anticipated motions. In the case of the ECG sensor package 300, the more adhesive hydrocolloid layers 412-418 make up the majority of the adhesion surface in a round/oval shape to accommodate motion from all directions.

Another challenge faced by sensor systems arises from the inherent properties of skin. In order to acquire data form a body surface for an extended period, the sensor system and related adhesive will be exposed to the intrinsic properties of the skin, such as oil secretions, perspiration, and hair. While skin preparation prior to application may alleviate some of the problems (e.g. hair), other properties of the skin should ideally be taken accounted for by the sensor system. By way of example, the sensor package 300 employs hydrocolloid layers 412-418 to absorb excessive oil and perspiration while maintaining the area moist for comfort. Materials with properties similar to hydrocolloid, such as hydrogel, could also be used. The protective layer 430, which can be made of polyurethane, provides water-resistance while remaining breathable, thus allowing the release of excessive moisture from the absorbent hydrocolloid layers 412-418 for the comfort of long-term wearing. Materials with similar properties, such as GoreTex® could also be used. A structural layer provided by the backers 442-448, which may be perforated PET, allows for maximum breathability through the protective layer 430. Further, in cases where the longevity of the adhesive on the body is less than the ideal wearing period, the adhesive electrode patch 400 is designed to be replaceable (e.g. via the implementation of snaps 450) and thus allows for the easy extension of the monitoring period, such as in the case of athletes, where sweating and movement can significantly shorten the life of the adhesive.

A fifth challenge faced by sensor systems is exposure to the physical environment. Placing sensors on a body can in turn create a set of challenges specific to the placement location. For example, temperature, humidity, the type of clothing/bedding and the amount of UV light the device will be exposed to, are all factors that can impact the usability of the sensor for the subject. Exposure to the physical environment can determine the longevity of the device on the body. Sensor packages in various embodiment address this issue by, for example:

1) Allocation of electronic components into multiple compartments 501-503. This relieves constraints on the device footprint and therefore allows the height of each compartment 501-503 to be minimized, which reduces the chances of that compartment 501-503 from getting caught on clothing, bedding or the like, or from otherwise being physically disturbed.

2) Use of smooth surfaces and corners. By designing the compartments to be smoothly rounded or to have rounded corners, the chances of the compartments 501-503 getting caught on clothing, bedding or the like is reduced.

3) Built-in stress relief In cases where the compartments 501-503 are caught on clothing, bedding or the like, the built-in stress relief (snaps 450, perforations 432, etc.) can decrease the chances for the device 300 to fail. The metal snaps 450 allow the electronics package 500 to detach from the adhesive electrode patch 400, and thus the subject's body, in situations such as under a strong tug from beddings, instead of breaking the device or adhesive. The metal snaps 450 also provide an easy and familiar means for subjects to reconnect the electronics package 500 to the adhesive electrode patch 400 and thus continue the monitoring regime.

4) Connectors to the adhesive electrode patch 400 (e.g. snaps 450) raise the electronics package 500 away from the body. This separation distance between the body of the subject and the electronics package 500 allows the electronics package 500 to cool, allows ventilation across the adhesive electrode patch 400, and prevents moisture accumulation between the adhesive electrode patch 400 and the electronics package 500.

5) Water resistance. The protective layer 430, which overlaps all the other layers below it and extends beyond them, forms a barrier layer that protects the adhesive electrode patch 400 from water damage.

6) Choice of materials. Rigid materials, such as for the shells 520, and flexible materials, such as for the substrate 510, can be tailored to their respective needs. For example, polycarbonate may be used for the shells 520, while TPE is used for the substrate 510, since both are low in UV-sensitivity, are non-reactive to water and oil, and are insensitive to temperature fluctuations within physiological ranges; these properties can help ensure the longevity of the device 300 on the body under normal usage. Of course, materials of similar or other desirable properties (such as silicone as a flexible material for substrate 510) can also be used.

Yet another challenge faced by sensor systems is to create and maintain specific environments for the sensors. After placement of a sensor system on the body, the device may not generate any meaningful data until specific environments for each sensor are created and maintained throughout the monitoring period. For example, electrical sensors require good conduction to the body, and optical sensors require close proximity to the skin. Sensor Packages in various embodiments address this issue by, for example:

1) The use of hydrogel, hydrocolloid, and polyurethane for the ECG electrodes 402-408. The hydrogel electrodes 402-408 provide a conductive path for ECG sensing. The hydrocolloid layers 412-418 absorb excessive moisture on the skin to help maintain the chemical composition of the hydrogel electrodes 402-408. The polyurethane protective layer 430 keeps the sealed compartment under the protective layer 430 moist so that the hydrogel electrodes 402-408 do not dry out and become non-conductive. The polyurethane protective layer 430 also allows the release of excessive moisture from the hydrocolloid layers 412-418 and hydrocolloid layers 412-418 that may otherwise affect the performance of the hydrocolloid layers 412-418. The polyurethane protective layer 430 is water-resistant such that external moisture (e.g. from showering) will not affect the electrical sensing environment maintained under the protective layer 430.

2) Maintaining skin contact. The use of biasing element 651-653 that push or bias the sensor 601-603 towards the skin of the subject ensure optimal sensing.

3) Insulation. In cases where sensors are closely spaced, sensors are preferably sufficiently insulated to prevent interference with each other. For example, in regions of the adhesive electrode patch 400 where two electrical sensors are closely placed, sweat accumulation can cause shorting of the two electrodes 406, 408. The hydrocolloid material 416, 418 between the two sensors 406, 408 helps to channel moisture away from the site; in addition, the closed cell foam strip 409 between the two electrodes 406, 408 acts as a moisture barrier. An optically absorbent foam material 660 can also be disposed between optical sensors to absorb any spillover light that may otherwise cause interfere between the sensors.

4) Signal monitoring. The sensing environment may degrade over time even when specific design elements implemented. The sensor packages 300, 600 can incorporate monitoring of the sensing environments such and can communicate wirelessly to the user/operator that the device 300, 600 is no longer working as intended. Examples of such monitoring systems include impedance and signal-to-noise ratio monitoring.

As previously indicated, another aspect of various embodiments of the invention is to provide for the synchronization or time-domain alignment between nodes for data collection purposes. For example, two, three or more ECG sensor packages 300 may be used by a subject. The data collected from these packages can, if properly synchronized or aligned, be used to generate data that is similar to the configuration of traditional 3-lead, 5-lead or 12-lead ECG leads. Of course, synchronization is not limited merely to ECG signals, and can be applied to any situation in which the data collected from one node is to be synchronized in time with data collected from another node. More specifically, in many applications it is desirable that synchronization of the timing of the samples across nodes be at a higher resolution than the sampling rate. For example, the sampling rate may be only 100 Hz, but it may be desirable that the samples be synchronized to within 1 mSec of each other, or even less. In such examples, exactly when a sample is taken may be of less importance than that the sample is taken within a certain time tolerance (e.g., 1 mSec, 1 µSec, etc.) of the other samples from the other nodes. To facilitate such synchronization or timing alignment, a master clock may be used to synchronize or align sample acquisition within a specified tolerance. In particular, one node in the network, such as the master node or a local device, may be used to generate a master clock signal that is used to synchronize or otherwise align sample acquisition times across all of the nodes.

By way of example, and with reference back to FIG. 1 (and considering the case in which each cluster 120, 130, 140 has only a single node), in one embodiment it may be desirable to wirelessly capture ECG signals from three sensor nodes 120-140, such as from three ECG sensor packages 300, on a subject and provide a composite waveform which is a combination of the signals from the three nodes 120-140. To do so, the signals from the nodes 120-140 are preferably aligned in time in a known manner to within +/−1 to 2 msec or even better, depending upon the processing that is subsequently performed on the collected data. Hence, it will be appreciated that other synchronization tolerances are also possible. Continuity of the data is also very desirable, as it is the combination of sensor information from all of the nodes 120-140 (i.e., from each of the three sensor packages 300) that is subsequently processed to generate corresponding ECG information.

The data collection circuitry in each sensor node 120-140 (i.e., within each sensor package 300) includes a clock that is used to determine the acquisition time and frequency of the samples. Typically, this clock is used to drive a programmable interrupt controller (PIC) to generate interrupts to a processor after predetermined durations, which causes the processor to collect and process another sample from the sensors 402-408. In order to achieve the above desirable features, the system should ideally correct for the differences in the PIC clocks and align in time the samples of the three sensor nodes 120-140, so that each of the samples in the three sensor nodes 120-140 occurs within 1 to 2 msec (or better) of the other samples. The PIC clocks can run at a frequency of, for example, 8 Mhz +/−20 ppm, although it will be appreciated that other frequencies and tolerances are also possible. This 20 ppm difference, although seemingly small, will cause the corresponding samples of the three sensor nodes 120-140 to drift apart unpredictably if not accounted for and corrected, especially in applications such as longer term continuous monitoring.

To ensure synchronization (i.e., an understanding of the time alignment of the collected data) of the nodes 120-140, in preferred embodiments network systems, the system establishes a periodic synchronization signal which is sent to the three sensor nodes 120-140 from, for example, the master node 110. It will be appreciated that another node 120-140, or another external device local to the nodes 120-140, could also generate the synchronization signal discussed herein, and that use of the master node 110 to generate the synchronization signal is simply one possible embodiment. Since only the relative time alignment of the samples is required, the accuracy of the synchronization signal is not necessarily as important as the repeatability and reliability of the signal. The three sensor nodes 120-140 can use the synchronization signal generated by the master 110 to accomplish three goals: (1) correct for differences in the PIC clocks, (2) chronologically align the samples in each data packet from the nodes 120-140 with each other, and (3) minimize radio congestion.

Figure 16:
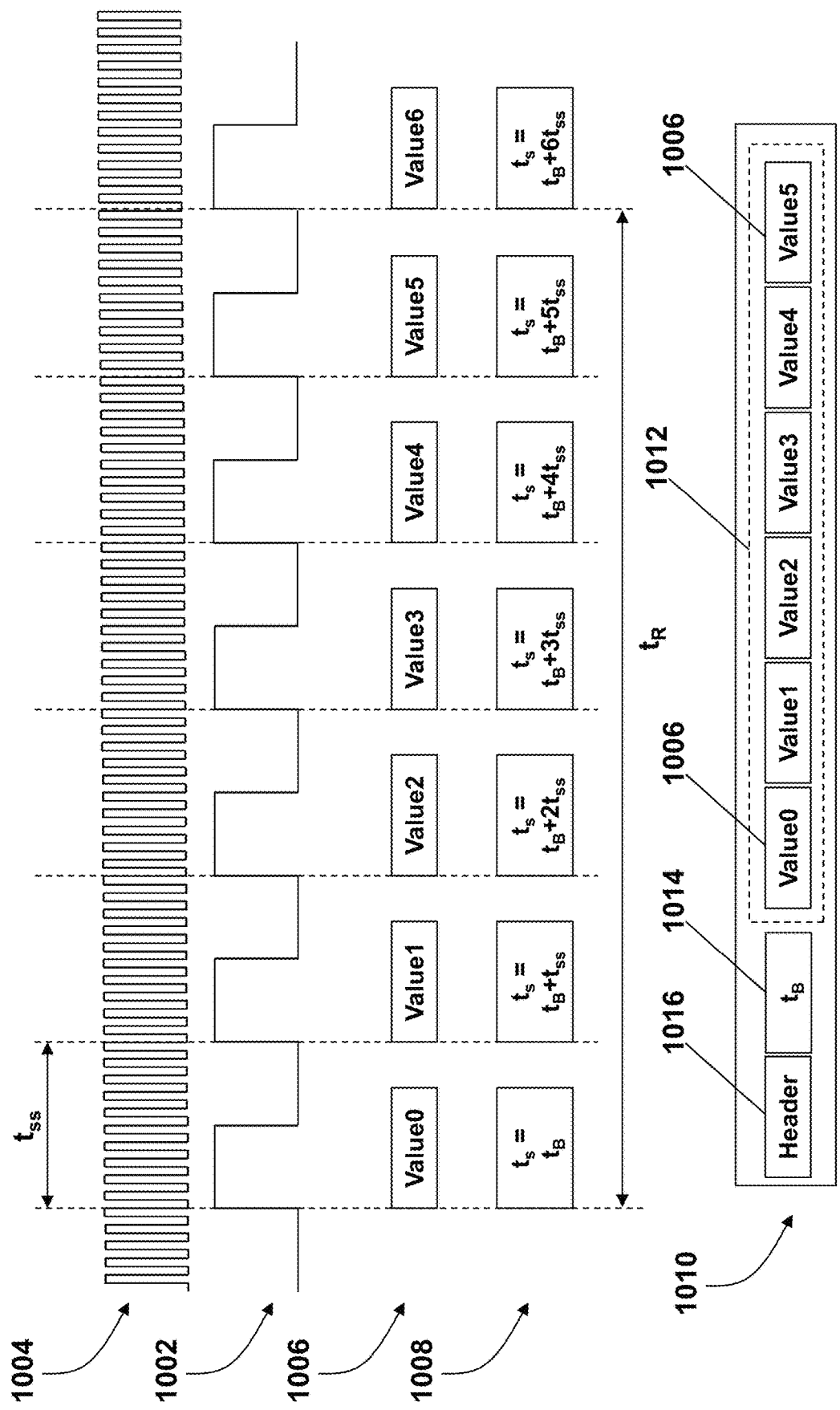
FIG. 16 illustrates timing of data collection performed by a node shown in FIG. 1 and the creation of a related data packet.

FIG. 16 illustrates the sample acquisition process respectively performed by each node 120-140. By way of example, each sensor node 120-140 may take samples from a subject at a desired sampling frequency $f_s$, such as 200 Hz. The desired sampling frequency fs may be preset for the system as a whole or may be programmatically set, such as by the master node 110 using any suitable signaling between the master node 110 and the other nodes 120-140. Each node 120-140 thus generates a stream of sample data points, each sample data point separated in time from the other by a sampling separation time of $t_{ss}=1/f_s$ seconds; in this example $t_{ss}=5$ msec, so that each sample data point would be separated from the next in time by 5 msec. Each sample data point thus has a sample value and a corresponding sample time $t_s$. A plurality of these sample values may then be arranged in a packet 1010, and at periodic reporting intervals one or more of these packets 1010 can be sent out to the master 110. For example, if the reporting interval is 250 msec, then every 250 msec each sensor node 120-140 may send one or more packets 1010 to the master node 110. Hence, to ensure that all sample values are sent to the master node 110, each packet 1010 should contain, in this embodiment, at least 50 sample values.

In addition to carrying sample values, each packet 1010 may also carry timing data indicating when the respective sample values were taken. For example, the packet 1010 may contain 50 sample values and 50 respective sample times $t_s$. Or, if it is assumed that the sample values are arranged in the packet 1010 in a predetermined manner, such as from earliest in time to latest in time, then the packet 1010 may simply carry the sample time of one of these sample values, such as the earliest in time, and the others can then later be determined based upon their respective positions in the packet 1010 in relation to the sample value having the given time. Or, the packet 1010 may simply indicate the reporting period in which the sample values were generated, and it is then assumed that the packets are arranged in a predetermined order with respect to a time defined within the reporting period, such as the start of the reporting period.

By way of example, and as shown in FIG. 16, each sensor node 120-140 may have a sample clock 1002 which is based off of a higher-frequency base clock 1004, such as the PIC discussed above. Hence, it will be appreciated that a "clock" does not necessarily require a respective oscillator or the like, but could be a device which triggers based upon events received from another device having such an oscillator. For example, the base clock 1004 may include, amongst other circuits, an 8 MHz oscillator, and the sample clock 1002 may be provided by dividing the base clock 1004 by 40,000 to get a sample separation time $t_{ss}$ of 5 msec. Any suitable circuit may be used to do this as known in the art, such as using a counter or the like. For example, every 80 clock ticks of the 8 MHz oscillator may cause the base clock 1004 to trigger an interrupt for the CPU in the node 120-140, which then increments a counter or value in memory. Once this counter or value achieves a certain sample count value, in this example a value of 500 to achieve the desired 5 msec sample separation value $t_{ss}$, the CPU may then cause a reading to be obtained to generate a sample data point and then resets the counter or value to zero. Any other suitable arrangements are possible, however, as known in the art. For example, synchronization based upon a clock in the ADC in the node 120-140 is also possible and applicable to the following.

Logically, as illustrated in FIG. 16, each sensor node 120-140 can be viewed as taking a sample on, for example, the rising edge of the sample clock 1002 to generate a sample value 1006 on each rising edge of the sample clock 1002. Each sample value 1006 has a corresponding sample time $t_s$ 1008, which corresponds to its respective rising edge of the sample clock 1002 and which may be based off of a base time $t_B$. It will be appreciated that time, as measured from the base time $t_B$, may be measured as actual time values in units of seconds, or in logical time values (e.g., "clock ticks") based off of any suitable reference, such as sample clock 1002 or, more preferably, base clock 1004 (thus providing for finer-grained resolution of each sample time $t_s$). It will be further appreciated that the sample clock train pulse 1002 may, in actual implementation, be instead implemented by the use of sample count values as discussed above, which is simply indicated logically in the figures as a square pulse train 1002.

After a sufficient number of samples 1006 have been taken for the reporting period $t_R$, the sensor node 120-140 constructs a data packet 1010 containing a data field 1012 holding the sample values 1006 (or information indicative thereof) in the reporting period $t_R$ and a time value 1014 indicative of the sample time $t_s$ 1008 of the first sample 1006 in the reporting period $t_R$, or even of each respective sample value 1006 in the data packet 1010. This time value(s) 1014 may be the actual sample time(s), such as the base time $t_B$ depicted in FIG. 16, or may be a value indicative of another time, such as a sequence number that the master node 110 can use to determine the reporting period $t_R$ that the data packet 1010 corresponds to. The data packet 1010 may also include a header 1016 containing other information, such routing information, an indicator of the packet type, status information of the node 120-140 (e.g., battery health), and the like, as known in the art. The data packet 1010 is then sent to the master node 110 where the sample data 1012 can be processed with reference to their respective sample times $t_s$, as computed from the time value(s) 1014 carried in, or otherwise indicated by, the data packet 1010. Simply by way of example, for sample data 1006 located at a position "n" within data field 1012 of data packet 1010, the corresponding sample time $t_s$ for that sample data 1006 may be computed as $t_s=t_B+n*t_{ss}$, in which $t_{ss}$ is the sample separation time, and with the first sample value 1006 having a sample time $t_s=t_B$, as provided by time value 1014, and understood to have a position n=0 in the data packet 1010. Of course, other logical arrangements are possible.

Figure 17:
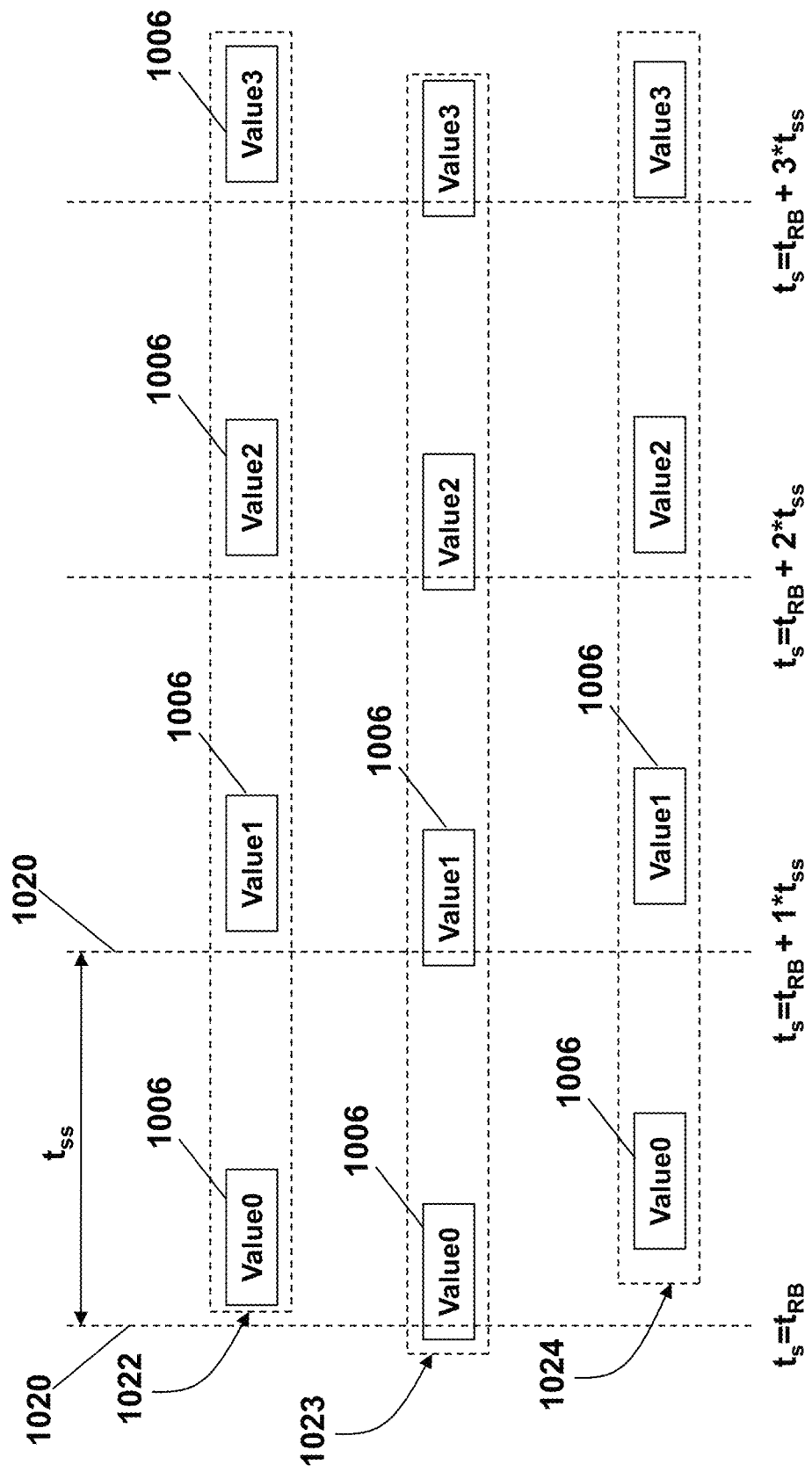
FIG. 17 illustrates possible data synchronization issues when receiving data streams from multiple data sources having different sampling clocks.

In various embodiments, it is desirable that the master node 110, or any computing device to which the master node 110 is connected and providing data, be able to understand how the sample times $t_s$ of the sample values 1006 in the data packets 1010 respectively received from the nodes 120-140 correspond to each other in time so that processing of the sample data 1006 can be performed to obtain medically useful information. By way of example, and with further reference to FIG. 17 that illustrates synchronization problems between samples 1006 across different nodes 120-140, suppose the master node 110 wishes to collect data values 1006 at specific desired times 1020 within a reporting period $t_R$, these desired times 1020 regularly separated from each other by a sample separation interval $t_{ss}$, and which can be respectively given as $t_{RB}+n*t_{ss}$, in which "n" is an interval ranging from 0 to N−1, with "N" being the total number of samples 1006 in the reporting period $t_R$, and $t_{RB}$ is the base time at which the reporting period $t_R$ begins. Sensor nodes 120-140 are disposed on the subject, and ideally send respective data streams 1022-1024 in the form of corresponding data packets 1010, in which each data value 1006 in the data packet 1010 is aligned with a corresponding desired time 1020. However, due to drifting of their respective clocks, as shown in FIG. 17, this ideal is typically not met and the data values 1006 of the data streams 1022-1024 are not aligned with the desired times 1020 of the master node 110, or even with each other. For example, each sample value 1006 of data stream 1022 from node 120 lags slightly behind the desired times 1020. The first data value 1006 of data stream 1024 from node 140 lags behind that of data stream 1022 and, moreover, each successive data value 1006 in data stream 1024 is successively closer to the corresponding desired times 1020, indicating that the sample separation time of data stream 1024 does not equal the sampling separation time $t_{ss}$ expected by the master node 110. Data stream 1023 from node 130, on the other hand, is early, with each data value 1006 having been sampled slightly before the corresponding desired time 1020. The phase and frequency of the data streams 1022-1024 can thus be out of alignment with the phase and frequency of the data collection times 1020 desired by the master node 110. Yet, to develop medically relevant information, it is often desirable to understand how the sample times $t_s$ of the respective data values 1006 correspond to the desired times 1020, to the sample times $t_s$ of the corresponding data values 1006 in the other data streams 1022-1024, or both.

To facilitate such an understanding, in preferred embodiments a synchronization device, such as the master node 110, broadcasts synchronization packets to the sensor nodes 120-140 at periodic intervals. Preferably, a multicast protocol is used so that each sensor node 120-140 receives the same synchronization packet at substantially the same time as the other sensor nodes 120-140. Each synchronization packet may include, for example, a sequence number, a time value or both. The sequence number may be used to identify, for example, a reporting period $t_R$ associated with that synchronization packet. Any suitable time interval may be used to successively transmit the synchronization packets, but it is preferred that this time interval is constant. In a specific embodiment, the time interval is set equal to the reporting interval $t_R$. The synchronization packet may be transmitted, for example, a predetermined time before the next reporting period $t_R$, such as 25 msec (before), 0 msec (start of), −25 msec (after), etc., and the sensor nodes 120-140 can make use of this predetermined time when calculating phase shifts as discussed in the following. Using these synchronization packets, the sensor nodes 120-140 are able to provide the time value 1014 in each data packet 1010 that they transmit to the master node 110, which allows the master node 110 to thereafter determine the respective sample times $t_s$ at which each sample value 1006 was collected.

Figure 18:
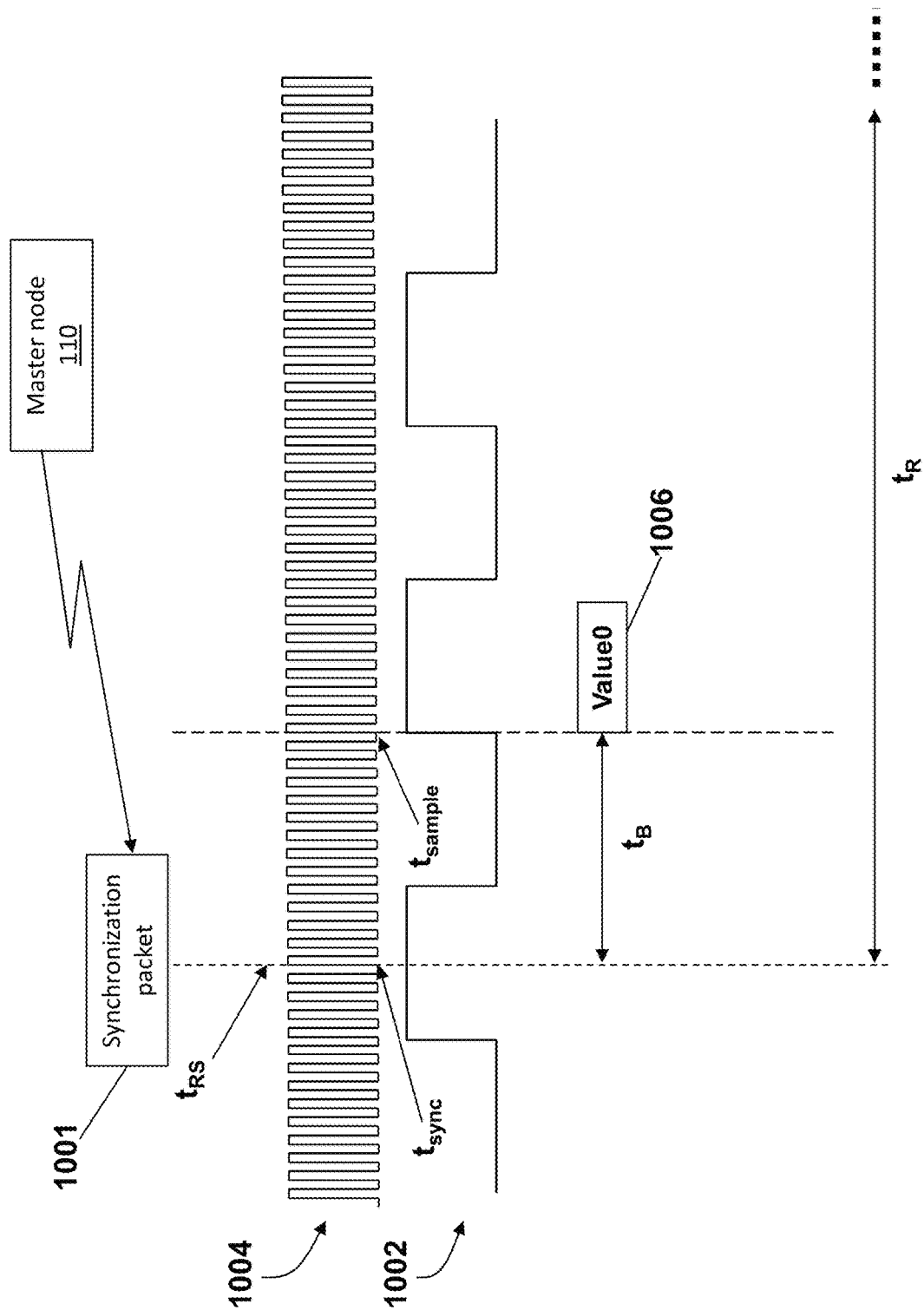
FIG. 18 illustrates determination of a phase offset of a sample value from a desired sampling time.

By way of a first specific example, and with reference to FIG. 18, the master node 110 may transmit a synchronization packet 1001 at the very beginning point $t_{RS}$ of each reporting period $t_R$, in which each reporting period $t_R$ is a fixed length, such as 250 msec. Hence, every 250 msec, the master node 110 transmits a synchronization packet 1001 marking the beginning time $t_{RS}$ of that reporting period $t_R$. The synchronization packet 1001 may include a sequence number or the like identifying the specific reporting period $t_R$ being marked. Upon receipt of the synchronization packet 1001, each sensor node 120-140 immediately references its high frequency base clock 1004 to determine the time $t_{sync}$ reception of the synchronization packet 1001, and records in its memory this time $t_{sync}$, together with the corresponding sequence number or like within the synchronization packet 1001 identifying the specific reporting period $t_R$. Because the sample clock 1002 can be determined by the base clock 1004, each sensor node 120-140 can determine a time $t_{sample}$, in terms of the base clock 1004, that the first sample value 1006 (indicated in the figure as "Value0") will be obtained in that reporting period $t_R$. The phase difference $t_B$, then, between when the first sample 1006 is actually taken by the node 120-140 as compared to the time $t_{RS}$ the master node 110 actually wanted this sample 1006 taken is thus simply $t_B=t_{sample}-t_{sync}$, and can be negative or positive depending on whether the first sample 1006 in the reporting period $t_R$ lagged or preceded the desired sampling time at tRS. This value $t_B$ can then be provided as the time value 1014 in the data packet 1010 for the reporting period $t_R$. Each subsequent data value 1006 in the data field 1012 can then be assumed to have a corresponding sampling time of $t_s=t_B+n*t_{ss}$, as previously discussed.

Using interpolation of sample values 1006 around the respective desired sampling times 1020, the master node 110 can, for example, determine or extrapolate what the sample values 1006 received from each sensor node 120-140 should be at these desired times 1020, or at other nearby times, and use this extrapolated information to thereafter generate medically useful information. Any suitable interpolation methods may be used to derive a computed sample value at each of the desired sample times 1020 (or other times) using the collected sample values 1006 and knowledge of their respective chronological times is in relation to the desired sample times 1020, such as linear interpolation, polynomial interpolation and the like.

As previously noted in relation to the hypothetical data stream 1024 of FIG. 17, the sampling clock 1002 of a sensor node 120-140 can be out of frequency with the desired sampling frequency $f_s$. Hence, in addition to computing a numerical value $t_B$ indicating how far out of phase each data stream 1022-1024 is from the desired sampling times 1020, in preferred embodiments each sensor node 120-140 also uses the synchronization packets 1001 to adjust the timing of its respective sampling clock 1002 to provide improved frequency locking between the sampling clock 1002 and the desired sampling frequency $f_s$. To facilitate such frequency locking between the master node 110 and the sensor nodes 120-140, in preferred embodiments the sensor nodes 120-140 monitor the amount of time elapsed between successive receipts of synchronization packets 1001 and use this time to determine a proper devisor or count value of the base clock 1004 to use to trigger a sampling time for the sampling clock 1002.

Figure 19:
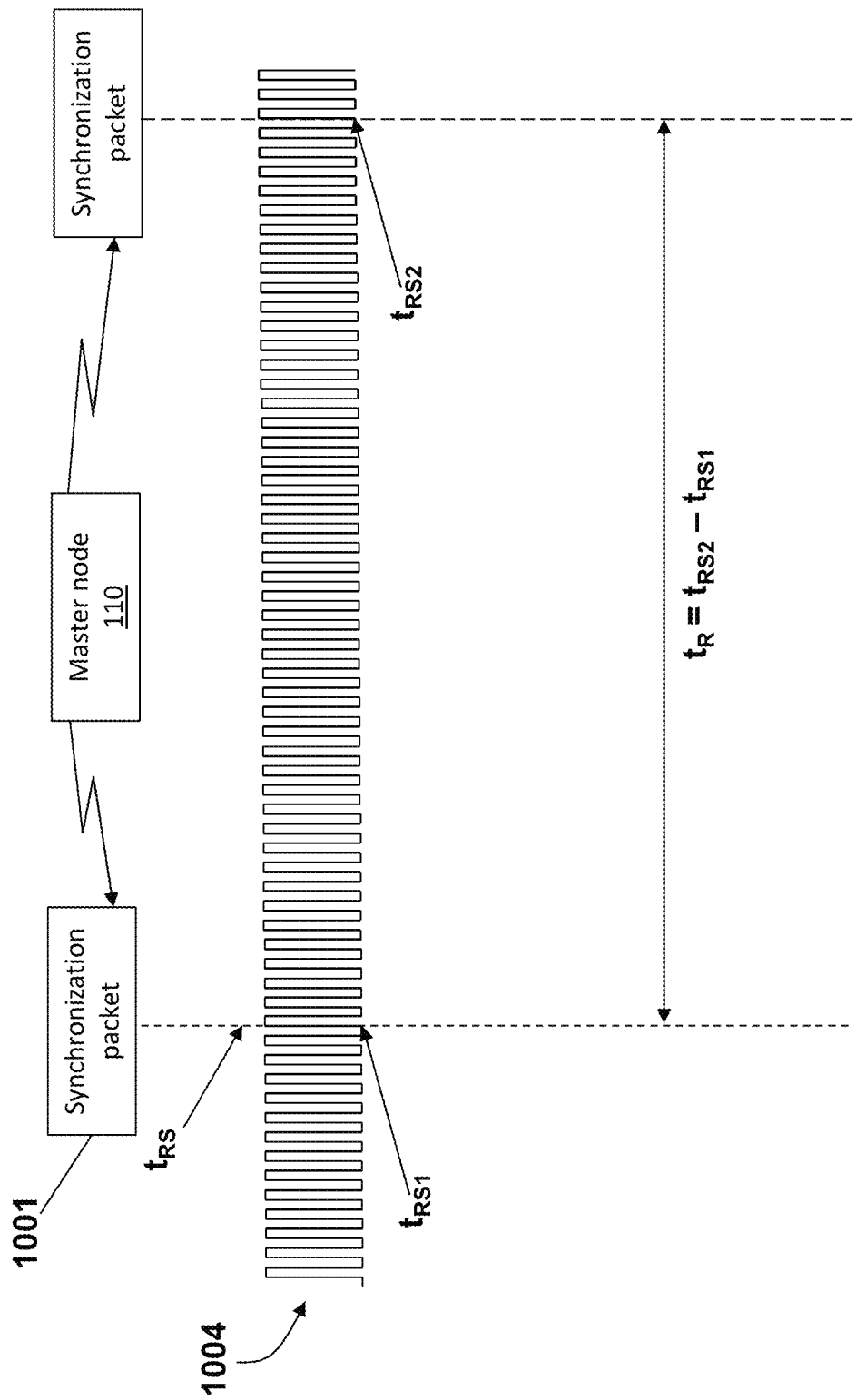
FIG. 19 illustrates timing of the width of a reporting period using synchronization packets transmitted by a master node depicted in FIG. 1 and a timer present in a data collection node receiving the synchronization packets.

For example, and with additional reference to FIG. 19, suppose the base clock 1004 has a frequency of $f_B$, which is significantly greater than the desired sampling frequency $f_s$, such as five or more times greater, more preferably 40,000; 80,000; 100,000 or more times greater than $f_S$ Further suppose that there are N samples per reporting period $t_R$, and that synchronization packets 1001 are sent at the beginning of each reporting period $t_R$. Upon receipt of a first synchronization packet 1001, the sensor node 120-140 obtains the time of receipt $t_{RS1}$ of this first synchronization packet 1001 as measured by its base clock 1004. Upon receipt of an immediately subsequent second synchronization packet 1001, the sensor node 120-140 obtains the time of receipt $t_{RS2}$ of this second synchronization packet 1001. The duration of the reporting period $t_R$, as measured by the base timer 1004 of the sensor node 120-140 is thus $t_{RS2}-t_{RS1}$. The sample separation time $t_{ss}$ between subsequent data points, as measured by the base clock 1004 of the sensor node 120-140, is then $(t_{RS2}-t_{RS1})/N$. The sensor node 120-140 then uses its base clock 1004 to generate the corresponding sampling clock 1002 having a sample separation period $t_{ss}=(t_{RS2}-t_{RS1})/N$. This can be done by any suitable method. For example, the sensor node 120-140 can monitor the count value of the base clock 1004, such as by suitable programming of the PIC, to trigger a sampling event for sample value "n" (i.e., corresponding to the rising edge of the sampling clock 1002 depicted in the figures) when the count value of the base clock 1004 equals $t_c+n*t_{ss}$, in which $t_c$ is a constant integer value (and could be zero), and n is an integer value $0 \le n \le (N-1)$.

In preferred embodiments, when first synchronizing with the master node 110, the sample separation period $t_{ss}$ is computed over a plurality of reporting periods $t_R$ and then averaged, such as over four or more reporting periods $t_R$. Additionally, the value $t_c$ is then preferably adjusted so that the time interval $t_B$ (i.e., phase shift) between when a sample value 1006 is taken and the desired time 1020 for that sample 1006 is zero or at least minimized. By way of example, when powering up, each sensor node 120-140 may first wait to receive a predetermined number of contiguous synchronization packets 1001 (which can be determined by, for example, the sequence numbers in the synchronization packets 1001 or by a priori knowledge of the expected separation time $t_R$ between the synchronization packets 1001). These received synchronization packets 1001 are used to generate an average value for the sample separation period $t_{ss}$ as measured from the base clock 1004 of that sensor node 120-140, as discussed above. Then, each sensor node 120-140 can assume that $t_c$ is zero and measure the resultant respective phase shift $t_B$ for that node 120-140, which can be averaged over one or more additional reporting periods $t_R$. Once this average phase shift $t_B$ is known, the respective count values for the sample times 1002 of the sensor node 120-140 can be measured off of the base clock 1004 of the sensor node 120-140 as $(n*t_{ss})-t_B$.

Preferably, each sensor node 120-140 continuously monitors the incoming synchronization packets 1001 and adjusts its count value for the sample separation period tss and, optionally, the phase offset value tB, thus providing a phase lock loop ("PLL") of the sample times is based upon the received synchronization packets 1001. If all of the sensor nodes 120-140 implement such PLL logic (either in hardware, software or combinations thereof), the master node 110 can assume that the sample data values 1006 carried in the data field 1012 of a data packet 1010 are properly synchronized to the desired sample times 1020 for a reporting period tR as determined by the master node 110 via the synchronization packets 1001. Hence, time synchronization of the data values 1006 across all data packets 1010 from all sensor nodes 120-140 may then simply involve nothing more that correlating, for example, data packet 1010 sequence numbers with each other.

For example, in response to a synchronization command broadcast from the master node 110, all of the sensor nodes 120-140 may reset their data packet 1010 sequence numbers to a predetermined value, such as zero. Thereafter, the master node 110 may assume that data packets 1010 received from the sensor nodes 120-140 having the same sequence numbers contain sample data 1006 for the same reporting period $t_R$, all of which is aligned on the correct desired sample times 1020. Hence, in preferred embodiments, the time value 1014 in each data packet 1010 is simply a sequence number that can be correlated against corresponding sequence numbers in data packets 1010 from other sensor nodes 120-140 to determine the reporting period $t_R$ to which each data packet 1010 corresponds.

Alternatively, each sensor node 120-140 may explicitly include the sequence number received from a synchronization packet 1001 marking, for example, the start of a reporting period $t_R$ to indicate this reporting period $t_R$ to which the data packet 1010 corresponds.

As noted above, in various embodiments, each sensor node 120-140 implements a PLL, such as in software, to ensure synchronization in frequency and phase of their respective sample clocks with the synchronization packets 1001 transmitted by the master node 110. It will be appreciated that phase and frequency locking with the synchronization packets 1001 can be maintained by continuously adjusting the frequency of the sampling clock, which is determined, with reference to the above embodiments, by $t_{ss}$, in which each sample is separated from its immediate neighboring samples by $t_{ss}$ ticks of the base clock 1004. When it is determined that the sampling speed is too slow as compared to the synchronization packets 1001, the value of $t_{ss}$ can be reduced, thus increasing the sampling frequency. Similarly, when it is determined that the sampling speed is too fast as compared to the synchronization packets 1001, the value of $t_{ss}$ can be increased, thus reducing the sampling frequency. The PLL logic continuously monitors the sampling times against the synchronization packets 1001 and adjusts the value of $t_{ss}$ so as to maintain both frequency and phase locking with the synchronization packets 1001.

In preferred embodiments, when a node 120-140 is first establishing communications with the master node 110, the value of $t_{ss}$ (i.e., the sampling frequency) can be changed relatively abruptly by using computed values, as discussed earlier with reference to FIG. 19. However, once communications and synchronization has been established with the master node 110, it is preferred that the value of $t_{ss}$ is thereafter changed only by predetermined increments (or decrements) rather than abruptly by using computed values. For example, the predetermined increments may be ±3, ±2 and ±1. Depending on how far out of phase the sampling clock is with the synchronization packets 1001, $t_{ss}$ may be incremented (or decremented) by one of these predetermined increments. These increments are preferably no greater than one part in 1,000 of the base clock 1004, more preferably no more than one part in 5,000 of the base clock 1004, more preferably still no more than one part in 10,000 of the base clock 1004. Hence, when an established communication link is present between the node 120-140 and the master 110, the sampling frequency $t_{ss}$ does not change abruptly, but instead slews slowly up or down—or not at all, when properly locked. This gentle slewing of the sampling frequency $t_{ss}$ ensures that the sensors 120-140 remain substantially locked, over long time periods, with the synchronization packets 1001, which avoids potential timing jittering that might otherwise come about from jittering in the base clocks of both the sensors 120-140 and the master node 110 itself.

Each sensor 120-140 can detect loss of communication with the master node 110 by noting that a synchronization packet 1001 has not arrived within an expected time window. The loss of one, two or some predetermined number of synchronization packets 1001 can then be interpreted by the sensor 120-140 as a communications failure with the master node 110. When communications is reestablished with the master node 110, the sensor 120-140 may reacquire sampling lock by, for example, directly computing a new value for $t_{ss}$ as described above in relation to FIG. 19, or may instead use more rapid slewing of the sampling frequency $t_{ss}$, such as slewing which is fives time or more greater than the slewing that occurs once communications have been established (e.g., increments of ±15, ±10 and ±5). This rapid slewing allows for more rapid frequency and phase locking with the synchronization packets 1001. Once an initial locking has occurred, the slew rate may then be adjusted downward to the nominal values discussed above to avoid jittering in the sample times.

In addition to using the synchronization packets 1001 to implement phase and frequency synchronization between the sensor nodes 120-140 and the master node 110, the synchronization packets 1001 can also be used to prevent data packet 1010 collisions, and thus facilitate more rapid communications between the sensor nodes 120-140 and the master node 110.

In a preferred embodiment, each sensor node is allocated to a respective cluster, as indicated in FIG. 1. For example, a first sensor "Node 1" may be allocated to Cluster A 120, a second sensor "Node 2" may be allocated to Cluster B 130 while third sensor "Node 3" is allocated to Cluster C 140. Allocation of the sensor nodes to their respective cluster assignments 120-140 can be performed, for example, by the master node 110 during an initialization step, in which the master node 110 instructs each sensor what its respective cluster 120-140 value is. Alternatively, the sensors may be preprogrammed with a respective cluster value. Internally within a cluster 120-140, a single sensor node may be elected, assigned or preprogrammed to communicate data collected in that cluster 120-140 to the master node 110.

Figure 20:
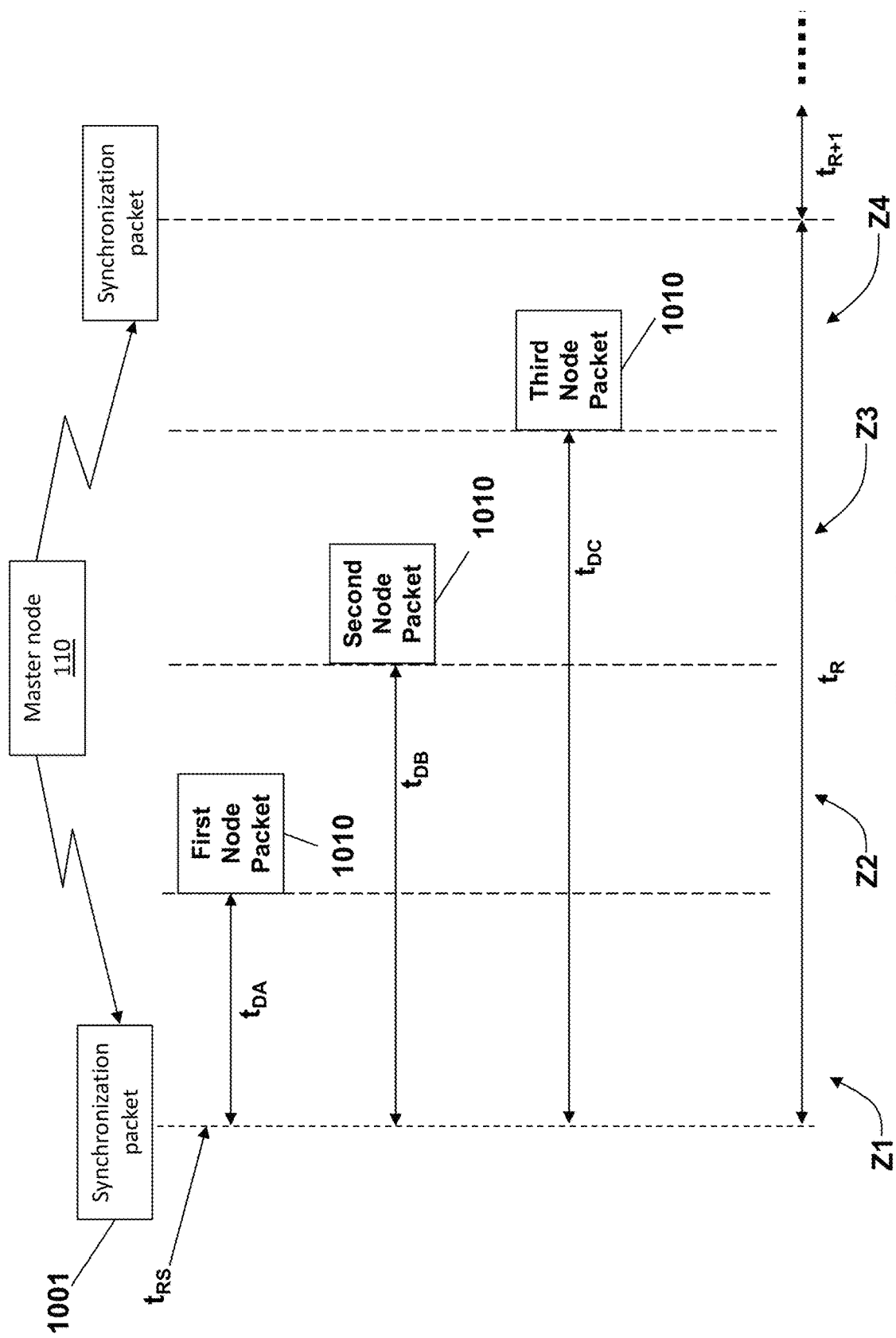
FIG. 20 illustrates using the synchronization packets transmitted by a master node to schedule data packet transmissions.
Figure 21:
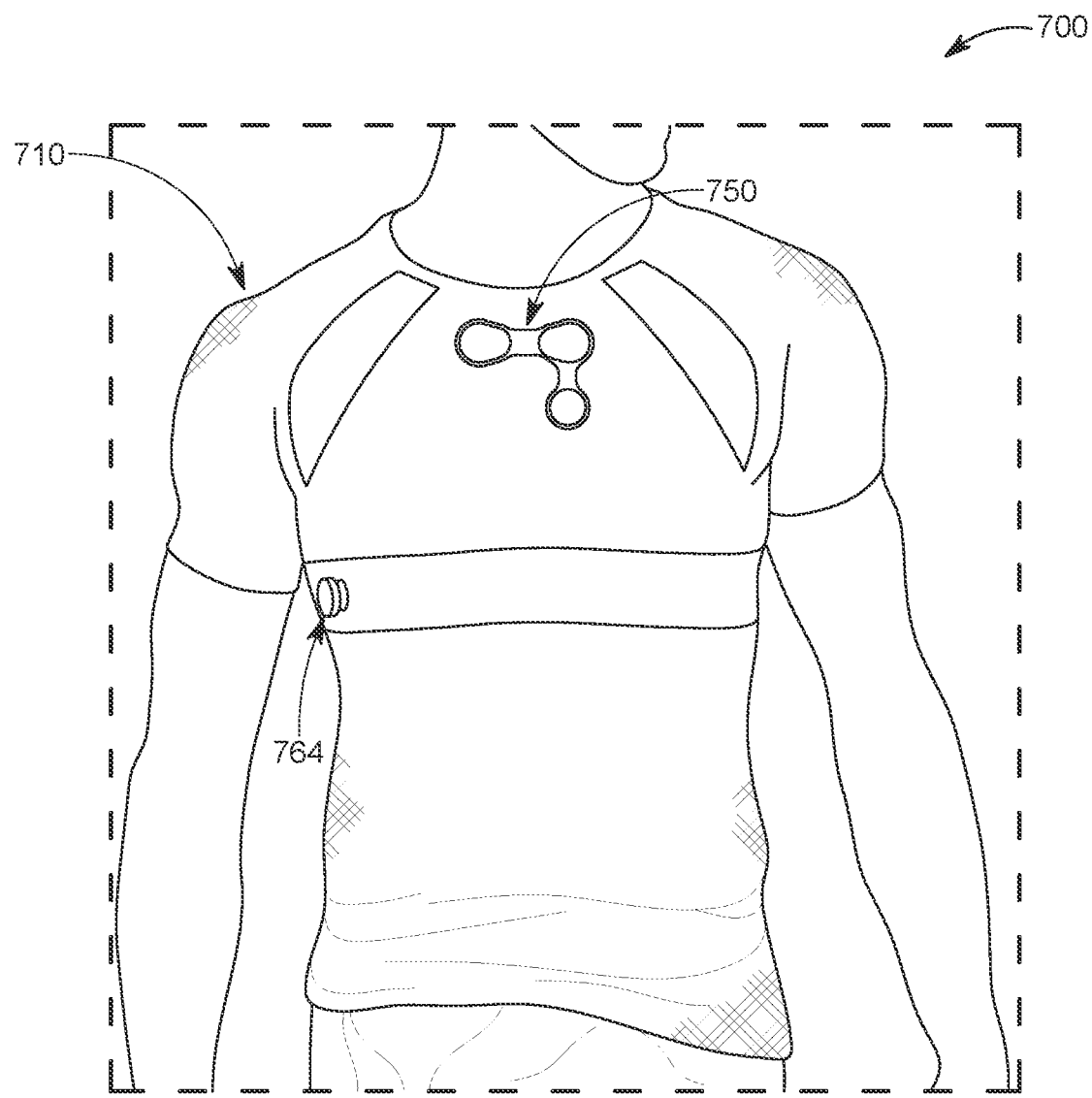
FIGS. 21-24 depict an embodiment garment system.
Figure 22:
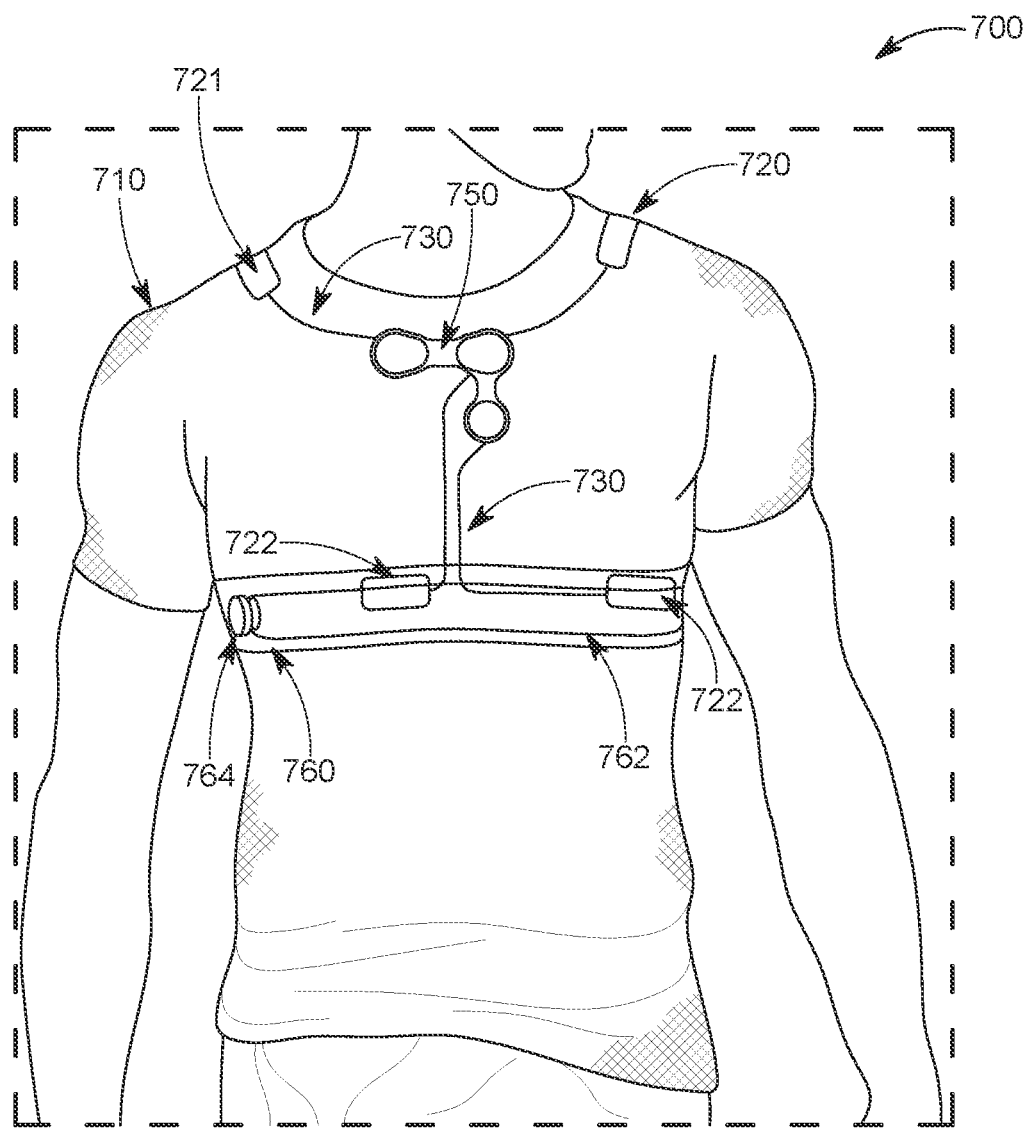
Figure 23:
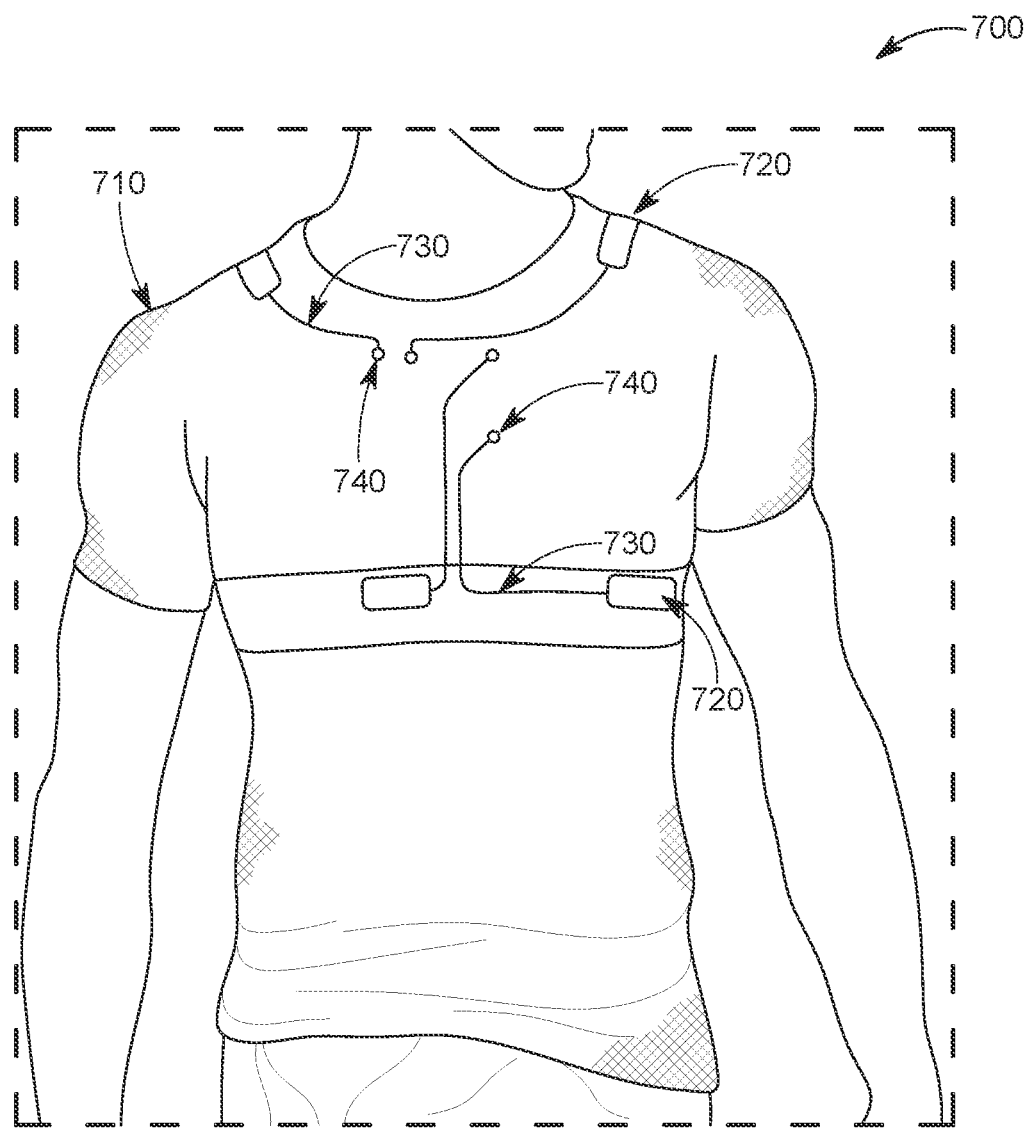
Figure 24:
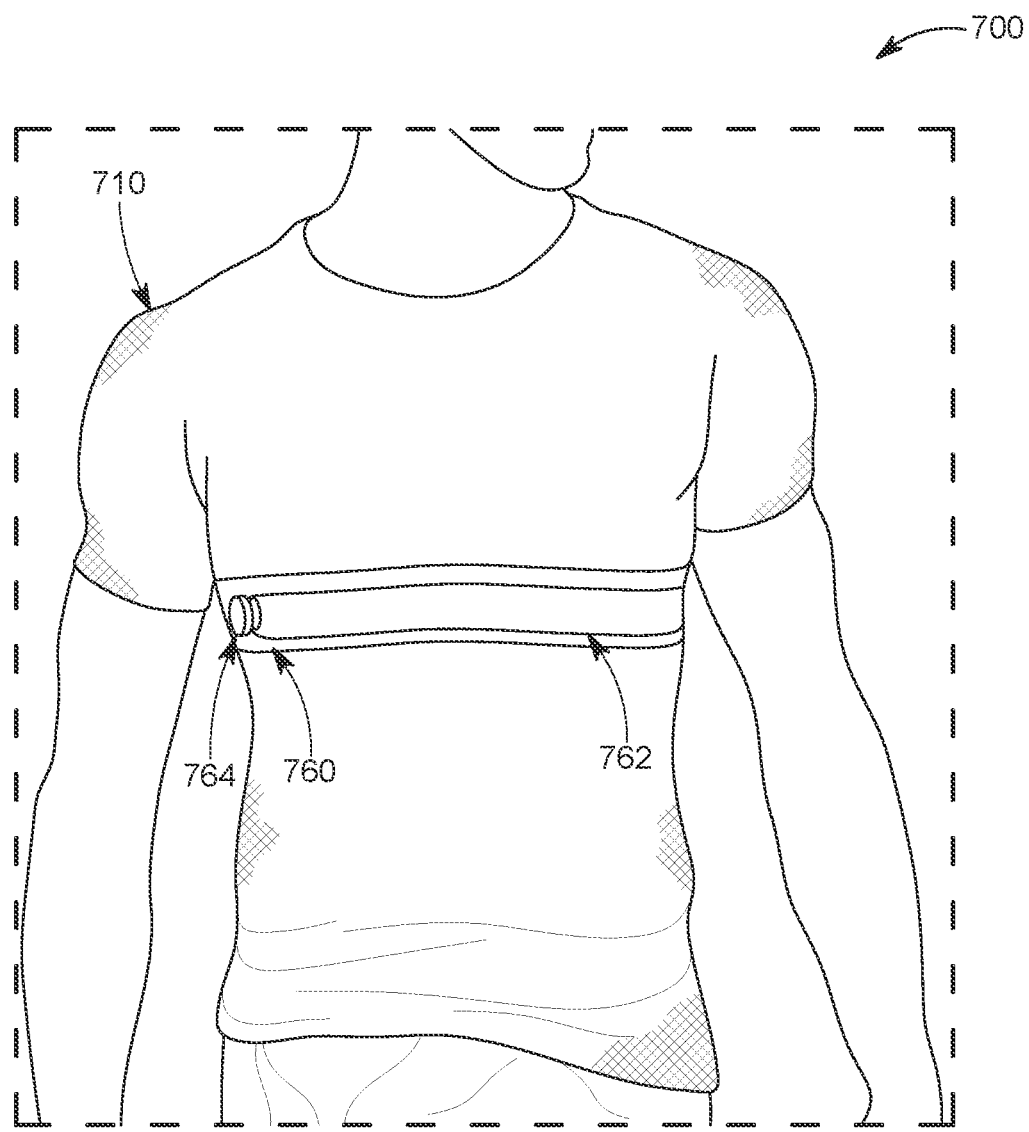

To provide for data packet 1010 collision avoidance, as illustrated in FIG. 20, each cluster 120-140 delays the sending of its respective data packets 1010 based upon its cluster assignment. The first cluster 120, assigned to Cluster A, delays by a time delay value $t_{DA}$, as measured from the point $t_{RS}$ of the reporting period $t_R$ as indicated by the synchronization packet 1001, such as by 60 msec. The second cluster 130 (Cluster B) delays by a time delay value $t_{DB}$, such as 120 msec, while the third cluster 140 (Cluster C) delays by toe, such as by 180 msec. Hence, in this specific embodiment, four 60 msec zones Z1-Z4 can be defined within, for example, the 250 msec reporting period $t_R$ defined between immediately adjacent synchronization packets 1001. These zones Z1-Z4 can respectively be used by the sensor nodes for synchronization Z1, transmission of data packets for nodes in Cluster A Z2, transmission of data packets for nodes in Cluster B Z3 and transmission of data packets for nodes in Cluster C Z4.

With data synchronization between the various nodes, the master node 110, or a computing device to which the master node 110 is connected and providing the sample values 1006 and related sample times $t_s$, can generate medically useful information that might not otherwise be possible if the data packets 1010 were not synchronized in time with each other in a known way. The following provides two non-limiting examples.

In the first example, two of the ECG sensor devices 300 are used, with one being placed centrally in the chest region, and the other laterally along the ribcage of the subject. With this arrangement, and the synchronization of data received by the two sensor devices 300, a 12 lead ECG system is made possible, also known as a Frank Lead System or an Orthogonal Electrocardiogram, as disclosed, for example, in http://circ.ahajournals.org/content/30/6/853.full.pdf. In various embodiments, the 3D electrical activity of the heart is reconstructed using three axes of information: x, y and z. The L-shape of the ECG sensor 300 disposed on the central area of the chest of the subject provides ECG information for the x and y planes. The additional ECG sensor 300 disposed along the ribcage of the subject provides the ECG information for the z direction, as known with the Frank Lead system. In particular, the predetermined direction of vectors represented by the potential differences measured by the ECG sensors 300 can be used to generate vectorcardiographic information, including standard ECG data currently used in medicine. Knowledge of the 3D electrical activity recorded in a synchronous manner by the sensors 300, together with the predetermined geometry and spacing of the electrodes in the sensors 300 as fixed by their respective substrates, is then used to mathematically convert that data back to standard 12-lead information that doctors are familiar with using any suitable method as known in the art, such as by way of Body Surface Potential Mapping (e.g. http://bio.felk.cvut.cz/biocmsms/index.php?page=bspm).

By way of another example, continuous blood pressure measurements can be developed using a single ECG sensor 300 in combination with the second embodiment sensor package 600, and more specifically, with the data developed by a plethysmographic sensor 603 which for this embodiment is placed on the subject's fingertip although as can be appreciated by one of ordinary skill in the art can be placed on other locations on the body. Hence, for this embodiment, it will be appreciated that the other sensors 601, 602 need not be used or even provided in the second device 600. The ECG sensor 300 and the secondary plethysmographic sensor 600 may be disposed on the subject as shown, for example, in FIG. 15. Initially, blood pressure data is obtained using a traditional arm cuff or other suitable method known in the art, and these readings are used for subsequent calibration purposes. Thereafter, synchronized ECG data and plethysmographic data are respectively obtained by the ECG sensor 300 and the secondary sensor 600. The plethysmographic data is used to provide information regarding the time when the pressure wave front of each pulse arrives at a specific location. The blood pressure ("BP") can then be calculated as follows.

Pulse transit time ("PTT") is first calculated, which can be defined as the time delay between the R-wave of the ECG signal obtained from the ECG sensor 300 and the arrival of the pulse wave in the periphery, as measured by the oxygen sensor 603 in the secondary sensor 600. The R-wave can be detected by any suitable method known in the art, such as by using amplitude and slope criteria or local maxima detection. The arrival of the pulse wave can be determined, for example, by the peak value of the differentiated plethysmographic signal, which corresponds to the steepest part of the ascent of the plethysmography signal. The pulse wave velocity ("PWV") can then be calculated according to the following formula:

$$PWV \text{ (cm/msec)} = BDC \times \text{height (cm)}/PTT \text{ (msec)},$$

in which BDC is a body correlation factor and height is the body length of the subject. The BDC can be determined experimentally, and is determined by the distance from sternal notch to the location of the secondary sensor 603. By adjusting the BDC, the secondary sensor 603 can be placed on different body parts depending on the need of the subject. For example, if the subject has a hand injury or other discomfort, the secondary sensor can be placed on the chest or shoulder.

The blood pressure BPcal is measured at a known calibration time "cal" using a conventional sphygmomanometer. A blood pressure $BP_{PTT,CAL}$ at this calibration time "cal" is then calculated as a function of PWV at the calibration time (i.e., using PTT as measured at the this calibration time "cal"), and can be given (when the secondary sensor 603 is placed on the fingertip) as:

$$BP_{PTT,CAL} = (P1 \times PWV(cal) \times \exp(P3 \times PWV(cal))) + P2 \times PWV(cal)^{P4},$$

in which PWV(cal) is calculated using the PTT at the calibration time "cal," "exp(x)" is the exponent function $e^x$, and P1-P4 are constants that can be experimentally determined, and can be, for example, P1=700, P2=766,000, P3=−1 and P4=9.

Thereafter, the blood pressure of the subject can be measured as a function of time at the desired time intervals 1020 by using PWV calculated at these desired time intervals I 020, according to the following formula:

$$BP_{PTT} = (P1 \times PWV \times \exp(P3 \times PWV)) + P2 \times PWV^{P4} - (BP_{PTT,CAL} - BP_{CAL}),$$

in which PWV is calculated at a time "t" to determined $BP_{PTT}$ at that time "t" by using "t" at a master synchronization time I 020 and corresponding ECG and blood oxygenation values I 006 at the synchronization time I 020 and synchronization times I 020 around it. By ensuring that the data collection nodes are properly synchronized with each other, it is thus possible to employ the above method. If the secondary sensor 603 is placed on other parts of the body, the mathematical relationship between the PMV and blood pressure can be modified per the initial measurement using a conventional sphygmomanometer as can be appreciated by one of ordinary skill in the art.

While the adhesive electrode patch discussed above can allow, for example, ECG signal collection on the body for extended periods of time, there are cases where the use of such implementations is prohibitive or undesirable. For example, some users may be allergic to the adhesive material used in the adhesive electrode patch, or certain athletes may find that their range of movement exceeds the tolerances of the adhesive electrode patch, or that excessive sweating may be detrimental to the adhesive patch. To address such issues, various embodiments allow for the integration of sensors embedded within a garment, to which an electronics package can then be coupled to monitor a physiological condition or conditions of the user. FIGS. 21-24 depict an embodiment utilizing garment system 700.

The garment system 700 includes a garment 710 as a basic substrate. Garment 710 can be made from any suitable materials, including natural fibers, such as cotton, synthetic fibers, such as nylon, or combinations thereof. Coupled to garment 710 are sensors 720, circuit traces 730 and snap parts 740. Snap parts 740 correspond to snap parts on an electronics package 750, and thus facilitate removable connection, both physically and electrically, of electronics package 750 to garment 710. Simply by way of example, electronics package 750 may be the same as, or similar to, the electronics package 500 discussed earlier, and snap parts 740 would then snap into snap parts 452 of electronics package 500.

Circuit traces 730 are coupled to garment 710 and each electrically connects a sensor 720 with a corresponding snap part 740. The circuit traces 730 can be formed from metal, such as copper, silver or the like, or any other suitable conductive materials including, but not limited to, conductive plastic, conductive ink and conductive fibers. Circuit traces 730 can be embedded into the basic substrate of garment 710, such as by weaving or the like, or can be embedded in or bonded to a secondary substrate, such as polyurethane or silicone, which is then bonded to the basic substrate of garment 710.

As noted above, on the output end, each circuit trace 730 terminates as a snap part 740 with the correct spacing so that it can directly connect to a corresponding snap part on electronics package 750. Thus, electronics package 750 can be used with an adhesive electrode, such as adhesive electrode patch 400, or with garment 710. On the input side, each circuit trace 730 electrically terminates at a respective sensor 720. It will be appreciated that circuit trace 730 may use a removable electrical connection to electrically connect to its respective sensor 720, such as the use of a snap connection analogous to that used for the electronics package 750; or, circuit trace 730 may be directly connected to sensor 720.

Each sensor 720 may be any type of sensor, including sensors based upon electrical characteristics, optical characteristics, thermal characteristics, chemical characteristics, or the like. Sensors 720 may be embedded within the substrate of garment 710, such as woven or sewn into garment 710, or may be bonded, for example, to the internal surface of garment 710. By way of a specific example, one or more of sensors 720 may be electrodes. Such electrodes can be formed as a stack of materials that includes an aqueous medium, such as hydrogel, similar to the adhesive electrode patch 400 described above, and can be coupled, preferably removably coupled, to the internal surface of garment 710 and respective circuit trace 730. Any suitable coupling mechanism(s) may be employed, such as glue, snaps, loop-and-hook fasteners, etc. Alternatively, such electrodes can be provided by a material or a combination of materials that are able to collect electrical signals from the skin without an aqueous interface ("dry electrodes"). Examples of such materials include silver, stainless steel, and conductive plastic. This material or materials may be, for example, woven or sewn into the fabric of garment 710; alternatively, such dry electrodes may also be removably coupled to garment 710 and the respective circuit trace 730.

By way of the specific example shown in FIGS. 21-24, the garment 710 may include four electrodes 720, including an electronic ground electrode 721 and three active electrodes 722, all of which are disposed on the internal surfaces of garment 710, or which are woven into the fabric of garment 710, in a manner suitable to establish electrical connection with the skin of the user. The electronic ground electrode 721 can be placed at any suitable location, including on the right shoulder or on the side of the torso. The three active electrodes 722 can be placed in specific places to obtain clinically relevant ECG signals. By way of example, one active electrode 722 can be placed on the left shoulder, another can be placed at or between the fourth or fifth intercostal space to the right of the sternum, and a third can be placed at the fifth intercostal space at the midaxillary line. Together, these locations of the three active electrodes 722 can provide ECG signals of Modified Chest Leads (mCL) 1 and 6, as well as Lead I. It will be appreciated that the active electrodes 722 can be placed at other specific locations to obtain other information corresponding to, for example, established ECG leads.

A potential challenge for acquiring sensor data using a garment, such as the garment 710, is ensuring the continuity and quality of the data received from the sensor 720. By way of example with electrodes, unlike an adhesive electrode, in which the contact with the skin is secured by adhesive, dry electrodes in a garment are more prone to movement and result in movement artifacts as well as discontinuation of the signal. To address this issue, various embodiments of the garment 710 include a tensioning system 760 that is designed to apply pressure to one or more of the sensors 720 to ensure that these sensors 720 remain firmly in contact with the skin of the user and keep movement or shifting to a minimum.

In certain embodiments, the garment 710 includes or is formed from an elastic material that creates compression to the body and thus actively pushes the sensors 720 towards the body; that is, the garment 710 may be made as elastic, skin-tight apparel. However, this may not be sufficient for some sensors 720. For example, the two active electrodes 722 on the chest may not be adequately pressed against the skin due to the elasticity of garment 710 alone. To ensure continuity and quality of the signals, tensioning system 760 may be used, which wraps around the chest to provide an additional force for securing the sensors 720 against the body. In one embodiment, tensioning system 760 includes tension wires 762, a pulley system that provides anchor points for tension wires 762, and a dial 764 for adjusting tightness. Tension wires 762 are preferably located over the sensors 720 to secure them to the body and extend around the pulleys. Dial 764 may be rotated to increase or decrease tension on tension wires 762, by, for example, spooling or unspooling tension wire 762 via the pulley system. However, any suitable tensioning system 760 may be employed to apply pressure onto one or more of sensors 720. For example, an elastic strap or drawstring in a casing may be used that can be pulled from one end to tighten garment 710; the elastic strap or drawstring can then be locked in its new position via snaps, buttons, spring locks, hooks, hook-and-loop fastener, etc. Alternatively, an inner compression layer can be used, which can be localized over the sensors 720 to be secured, in which the stretch of the fabric of garment 710 provides additional pressure against the sensors 720. By way of another example, and for the specific case of a sports bra, multiple adjustment locations for sizing the overall bra, including an adjustable chest strap and shoulder straps, may be used. The adjustments can be done, for example, by pulling a strap through a D-ring or other hardware and affixing it in place with loop-and-hook fastener or snaps; alternatively, such adjustment can be done with conventional lingerie hook-and-eye connections or hooks into pockets sewn into the fabric, analogous to those used on swimsuit tops.

Although tensioning system 760 is discussed above in relation to the chest under the sternum, it will be appreciated that it may be employed in other areas as well, such as over the shoulders. Such locations may be independently or collectively controlled, depending upon the embodiment of the design.

In various embodiments, by using the data transmission capability of the electronics package 750, the signal quality of the connection between each active sensor 722 and the user's skin can be assessed in real-time by software on an external device, such as a smartphone, master device 110, or the like, by any suitable measurements, such as by analyzing the signal-to-noise ratio ("SNR"), the impedance of the skin connection, noise analysis in the frequency domain, by visual display of a waveform for empirical judgment by the user (e.g. whether the waveform is smooth or not), etc. The external device can thus provide real-time feedback to the user, who can then adjust tensioning system 760 accordingly. For example, if the SNR is too low, the user may adjust tensioning system 760 to increase the tension on wires 762 and thus increase the pushing force of the active sensors 722 against the skin. On the other hand, if the SNR is sufficiently high, the user can adjust tensioning system 760 to relieve tension on wires 762 and thus relieve the user of any unnecessary discomfort. Together, this allows the user to achieve a balance between comfort and signal quality. In addition, tensioning system 760 can allow garment 710 to accommodate different body types and different movement requirements for different activities (e.g., running versus martial arts). Adjustable tensioning system 760 can be used multiple times at various locations where movement of sensors 720 is of concern. In some cases, where vigorous movement is expected, tensioning system 760 can be used together with adhesive-based sensors, such as adhesive electrodes, to ensure maximum signal quality and continuation.

Garment 710 is preferably washable. By way of example, for embodiments in which sensors 720 are removably coupled to garment 710, such as by way of snaps or the like, sensors 720 may be removed from garment 710 prior to washing. Garment 710 may also include a pouch into which electronics package 750 may be inserted, wholly or partly, which may protect electronics package 750 from physical disruption during exercise. Hence, some or all of snaps 740 may terminate within such a pouch. It will be appreciated that circuit traces 730 may be routed, and snaps 740 may be positioned, to support any desired location of electronics package 750 on garment 710. It will also be appreciated that garment 710 is not limited to the shirts and sports bras discussed above, but may also be used in, for example, hospital gowns, shorts, pants, socks, shoes and other types of clothing or apparel, and can thus facilitate collection of sensor data from any location on the body.

A benefit of various embodiments is that the same electronics package, such as electronics package 500 discussed above, may be used for both clinical use and consumer use. For example, in the clinical setting, a medical-grade wet electrode patch (e.g., an electrode patch conformal to ANSI/AAMI/EC12), such as adhesive electrode patch 400 discussed above, can be used to collect regulatory-approved (e.g., FDA-approved) ECG data, in combination with a corresponding electronics package, such as electronics package 500, which is itself ideally conformal to ISO-60601-2-47 standards to generate such clinical-grade ECG data. However, the same electronics package can then be repurposed for use in a garment, such as garment 710 discussed above, and use dry electrodes to collect ECG data for consumer use, which may not necessarily conform to the ANSI/AAMI/EC12 standards, but which can nonetheless generate data useful to the end-user, such as athletes interested in more accurate heart rate and rhythm data. The removable electronics package thus seamlessly and readily supports both consumer and clinical uses.

Moreover, as the electronics packages can support wireless communications with a master node, between themselves or both, the use of two or more electronics packages can be supported to generate additional sensor information. For example, two electronics packages 500 may be coupled to a garment, having a correspondingly suitable arrangement of sensors 720 and snap parts 740, to generate multiple channels of ECG data, which can be processed as discussed previously to generate 5- or 12-lead ECG data, such as via the Frank Lead System or an Orthogonal Electrocardiogram. By way of another example, one garment, such as garment 710, could be used to generate ECG data in conjunction with a first electronics package, while another garment, such as a sock, could by fitted with another type of sensor, such as a blood oxygen sensor, which, by way of a suitable snap or snaps, couples to another, smaller, second electronics package. The two electronics packages could wirelessly communicate with each other, or with a master node, to exchange their respective sensor information, as previously discussed, so that both ECG data and blood oxygenation data, can be generated in a seamless and convenient manner. Because sensors 720 can be removably connected to garment 710, different types of sensors, optionally, if necessary, in conjunction with different types of supporting electronics packages, can thus be used in a replaceable manner to readily generate multiple types of sensor information about a user.

The present invention is not to be limited in scope by the specific embodiments described herein. Various modifications of the invention in addition to those described herein will become apparent to those skilled in the art from the foregoing description and the accompanying figures.

One having ordinary skill in the art will recognize that the various mechanisms described for the preferred embodiments of the device may be adapted and interchanged between the preferred embodiments, without significantly impacting the structure and operation of the device. Use of the words "preferred embodiment" or "preferably" is not intended to imply that any other embodiment is less preferred or is not encompassed in the scope of the invention. Those skilled in the art will recognize that the present invention has many applications, may be implemented in many manners and, as such is not to be limited by the foregoing embodiments and examples.

Any number of the features of the different embodiments described herein may be combined into one single embodiment, the locations of particular elements can be altered and alternate embodiments having fewer than or more than all of the features herein described are possible. Functionality may also be, in whole or in part, distributed among multiple components, in manners now known or to become known.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention. While there had been shown and described fundamental features of the invention as applied to being exemplary embodiments thereof, it will be understood that omissions and substitutions and changes in the form and details of the disclosed invention may be made by those skilled in the art without departing from the spirit of the invention. Therefore, the appended claims are intended to cover conventionally known, future developed variations and modifications to the components described herein as would be understood by those skilled in the art.

We claim:

1. An electrode patch comprising:
   at least one electrode configured to contact a subject;
   a plurality of releasable electrical connectors electrically coupled to the at least one electrode, each one of the plurality of releasable electrical connectors is configured for electrical communication with an electronics package;
   an adhesive layer defining at least one aperture, wherein at least a portion of the at least one electrode is disposed through the at least one aperture of the adhesive layer, and wherein the adhesive layer is adapted and configured to adhere to the subject;
   a protective layer disposed over and covering the adhesive layer, wherein the protective layer defines a plurality of openings, wherein each one of the plurality of openings is dimensioned and configured for enabling disposing at least a portion of a respective one of the plurality of releasable electrical connectors therethrough;
   a plurality of active traces, including at least a first active trace proximal to the electronics package, wherein each of the plurality of active traces electrically connects a respective one of the plurality of releasable electrical connectors with the electronics package; and an open lead electrically connected to the first active trace, wherein the open lead is routed along and spaced a predetermined distance from a different active trace of the plurality of active traces, wherein the open lead has a free end terminating proximal to each of a different one of the plurality of releasable electrical connectors from that connecting to the first active trace.

2. The electrode patch of claim 1, including a backer disposed over the at least one aperture and at least a portion of the adhesive layer to provide structural strength thereto.

3. The electrode patch of claim 2, wherein at least a portion of one of the plurality of releasable electrical connectors includes a top portion and a bottom portion, wherein the backer is sandwiched between the top and bottom portions and the portions are coupled together.

4. The electrode patch of claim 2, wherein the backer is formed from a perforated polyethylene terephthalate or an ethylene-vinyl acetate/polyethylene blend.

5. The electrode patch of claim 1, wherein at least a portion of at least one of the plurality of releasable electrical connectors extends through the at least one of the plurality of openings.

6. The electrode patch of claim 1, wherein the protective layer is made from polyurethane with a moisture vapor transmission rate of about 300 to 1400 $gm/m^2/day$.

7. The electrode patch of claim 1, further comprising:
at least one additional electrode configured to contact the subject;
a plurality of additional releasable electrical connectors electrically coupled to the at least one additional electrode, wherein each of the plurality of additional releasable electrical connectors is configured for electrical communication with the electronics package;
an additional adhesive layer defining at least one aperture, wherein the at least one additional electrode is disposed within the at least one aperture of the additional adhesive layer, wherein the additional adhesive layer is adapted and configured to adhere to the subject; and
an additional protective layer disposed over and covering the additional adhesive layer, wherein the additional protective layer defines a plurality of openings, wherein each of the plurality of openings of the additional protective layer is dimensioned and configured for enabling disposing at least a portion of a respective one of the plurality of additional releasable electrical connectors therethrough.

8. The electrode patch of claim 7, including an isolating barrier disposed between the adhesive layer and the additional adhesive layer.

9. A method for obtaining physiological data from a subject, comprising:
adheringly disposing a sensor patch including a sensor on the subject, the patch configured to electrically couple at least one releasable electrical connector to the sensor;
physically electrically coupling an electronics package to the patch, the package including the at least one releasable electrical connector, wherein the at least one connector is coupled to an analog front-end circuitry configured to monitor a plurality of signal electrodes, wherein each one of the plurality of signal electrodes is electrically connected to the analog front-end circuitry via a respective one of a plurality of active traces, wherein the package is configured to generate physiological data corresponding to the subject and to wirelessly transmit the corresponding data to another device; and
equalizing an electronic noise signal between an active trace connecting a respective one of the plurality of signal electrodes with the analog front end circuitry and an open lead in electrical connection with said active trace at a confluence of each of the plurality of active traces with the analog front end circuitry, wherein the open lead is routed along and spaced at a predetermined separation from a different active trace, wherein the open lead has a length similar to a length of the different active trace, and wherein the active lead has a free end electrically isolated from each one of the plurality of signal electrodes different from the respective one of the plurality of signal electrodes.

10. The method of claim 9, wherein the sensor patch includes a plurality of sensors held by a release liner against the patch in a predetermined geometrical arrangement, wherein the method includes removing the release liner prior to disposing the sensor patch on the subject and prior to coupling the electronics package to the sensor patch.

11. The method of claim 10, wherein each one of the plurality of sensors is a corresponding one of an associated plurality of signal electrodes, wherein the geometrical arrangement approximates an L-shaped arrangement for the plurality of signal electrodes and the electronics package is configured to obtain electrocardiogram data from the plurality of signal electrodes.

12. An electronics package for a wireless physiological sensor system, comprising:
a substrate;
a patch configured to attach to a subject and including a plurality of sensors;
a plurality of electrical connectors on the patch and connected to the substrate;
a first shell and a second shell disposed and spaced apart on the substrate; and
an electronics package adapted and configured to monitor at least one of the plurality of sensors associated with physiological data corresponding to the subject and to wirelessly transmit the monitored data to a device, wherein the electronics package comprises:
a first electronics sub-system disposed in the first shell;
a second electronics sub-system disposed in the second shell, wherein the second electronics sub-system includes an analog front end circuitry configured to receive a physiological signal from each of the plurality of sensors to generate physiological data corresponding to the subject, wherein the first electronics sub-system includes a wireless transceiver to wirelessly transmit the corresponding physiological data to the device;
a first flexible electrical circuit electrically connecting electrical signals between the first and second electronics sub-system;
a plurality of active traces electrically connecting each one of the plurality of electrical connectors with the analog front end circuitry, wherein the plurality of active traces includes a first active trace and a second active trace; and
an open lead terminating proximal to a first one of the plurality of electrical connectors electrically connected to the first active trace, the second active trace electrically connecting a second one of the plurality of electrical connectors to the analog front end circuitry.

13. The electronics package of claim 12, wherein the substrate is flexible.

14. The electronics package of claim 12, wherein the first electronics sub-system is flexibly connected to at least one of the plurality of electrical connectors.

15. The electronics package of claim 12, wherein a length of the first electrical circuit between the first shell and the second shell is greater than a distance between the first shell and the second shell for accommodating stretching or flexing of the substrate.

16. The electronics package of claim 12, wherein at least a portion of the first shell and at least a portion of one of the plurality of electrical connectors is disposed in the substrate.

17. The electronics package of claim 12, wherein the analog front end circuitry comprises an amplifier, a band pass filter, and an analog-to-digital converter.

18. The electronics package of claim 12, wherein at least three of the plurality of sensors are arranged in an L-shaped configuration, the electronics package further including:
a third shell disposed on the substrate;
a third electronics sub-system disposed in the third shell;
a second flexible electrical circuit electrically connecting the second and the third electronics sub-systems;
wherein the first, second, and third shells are arranged in a substantially L-shaped configuration on the substrate with respect to the at least three of the plurality of sensors.

19. The electronics package of claim 18, wherein:
the first flexible electrical circuit comprises a first signal line extending between the first shell and the second shell;
the second flexible circuit comprises a second signal line extending between the second shell and the third shell;
the first flexible circuit further comprises a first open electrical line electrically connected to the second signal line and extending along the first signal line; and
the second flexible circuit further comprises a second open electrical line electrically connected to the first signal line and extending along the second signal line.

* * * * *